United States Patent [19]
Patton

[11] Patent Number: 5,859,335
[45] Date of Patent: Jan. 12, 1999

[54] ENHANCED BIOTIN BIOSYNTHESIS IN PLANT TISSUE

[75] Inventor: David Andrew Patton, Durham, N.C.

[73] Assignee: Novartis Finance Corporation, New York, N.Y.

[21] Appl. No.: 401,068

[22] Filed: Mar. 8, 1995

Related U.S. Application Data

[63] Continuation-in-part of Ser. No. 351,970, Dec. 8, 1994, abandoned.
[51] Int. Cl.$^6$ .............................. A01H 5/00; C12N 5/04; C12N 15/82
[52] U.S. Cl. ..................... 800/205; 435/69.1; 435/172.3; 435/419; 536/23.2; 536/23.6; 536/23.7
[58] Field of Search .......................... 800/205, DIG. 15, 800/DIG. 26, DIG. 43, DIG. 56, DIG. 58; 435/69.1, 172.3, 240.4, 320.1, 419; 536/23.1, 23.2, 23.6, 23.7

[56] References Cited

U.S. PATENT DOCUMENTS

| | | | |
|---|---|---|---|
| 5,096,823 | 3/1992 | Gloeckler et al. | 435/252.31 |
| 5,258,300 | 11/1993 | Glassman et al. | 435/240.4 |
| 5,445,952 | 8/1995 | Campbell et al. | 435/121 |

FOREIGN PATENT DOCUMENTS

| | | |
|---|---|---|
| 0635572A2 | 6/1994 | European Pat. Off. . |
| 2216530 | 10/1989 | United Kingdom . |
| WO94/08023 | 4/1994 | WIPO . |

OTHER PUBLICATIONS

Gerbling et al., "A new Acyl–CoA Synthetase, Located in Higher Plant Cytosol", *J. Plant Physiol.*, 143:561–564 (1994).
Van den Broeck et al., "Targeting of a foreign protein to chloroplasts by fusion to the transit peptide from the small subunit of ribulose 1,5–biphosphate carboxylase", *Nature*, 313:358–363 (1985).
Altschul, S.F. et al., "Basic Local Alignment Search Tool", *J. Mol. Biol.* 215:403–410 (1990).
Baldet, P. et al., "Biotin biosynthesis in higer plant cells Identification of intermediates" *Eur. J. BioChem.* 217:479–485 (1993).
Dickson et al., "Genetic Regulation: The Lac Control Region," *Science* 187:27–35 (1975).
Eisenberg, M.A., "Biotin: Biogenesis, Transport And Their Regulation", *Adv. Enzymol.* 38:317–372 (1973).
Eisenberg, M.A., "Regulation of the Biotin Operon in *E coli*", *Ann. N.Y. Acad. Sci.* 447:335–349 (1985).
Frigg, M., "Available Biotin Content of Various Feed Ingredients", *Poultry Science* 63:750–753 (1983).
Gloeckler, R. et al., "Cloning and characterization of the *Bacillus sphaericus* genes controlling the bioconversion of pimelate into dethiobiotin", *Gene* 87:63–70 (1990).
Knowles, J.R., "The Mechanism of Biotin–Dependent Enzymes", *Ann. Rev. BioChem.* 58: 195–221 (1989).
Kopinski, J.S. et al., "Biotin studies in pigs. 1. Biotin deficiency in the young pig", *British Journal of Nutrition*, 62: 751–759 (1989).

Kopinski, J.S. et al., "Biotin in Animal Nutrition", *Nutrition Reviews*, 48:352–355 (1990).
Levy–Schil, S. et al., "Biotin biosynthetic pathway in recombinant strains of *Escherichia coli* overexpressing bio genes: evidence for a limiting step upstream from KAPA", *Appl. Microbiol. Biotechnol.* 38:755–762 (1993).
Marshall, M.W., "The Nutritional Importance of Biotin—An Update", *Nutrition Today* Article 3: 26–29 (1987).
Newman, T. et al., "Genes Galore: A Summary of Methods for Accessing Results from Large–Scale Partial Sequencing of Anonymous Arabidopsis cDNA Clones", *Plant Physiol.* 106: 1241–1255 (1994).
Otsuka, A.J. et al., "The *Escherichia coli* Biotin Biosynthetic Enzyme Sequences Predicted from the Nucleotide Sequence of the bio Operon", *The Journal of Biological Chemistry* 263: 19577–19585 (1988).
Pai, C.H., "Mutant of *Escherichia coli* with Derepressed Levels of the Biotin Biosynthetic Enzymes", *J. Bacteriol.* 112: 1280–1287 (1972).
Robel, E.J., "The Value of Supplemental Biotin for Increasing Hatchability of Turkey Eggs", *Poultry Science* 70: 1716–1722 (1991).
Sakurai, N. et al., "Improvement of a d–biotin–hyperproducing combinant strain of *Serratia marcescens*", *J. Biotech.* 36: 63–73 (1994).
Shellhammer, A.J. Jr., "Analysis of a Biotin Auxotroph of Arabidopsis Thaliana", *Oklahoma State University Thesis* 1–134 (1986).
Shiuan, D. et al., "Transcriptional regulation and gene arrangement of *Escherichia coli, Citrobacter freundil* and *Salmonella typhiumurium* biotin operons", *Gene* 67: 203–211 (1988).
Stryer, L., "Amino Acid Biosynthesis is Regulated by Feedback Inhibition", *BioChemistry* 2: 505–503 (1981).
Watanabe, K. et al., "The Selection of Cultured Plant Cell Lines Producing High Levels of Biotin", *Phytochemistry* 21:513–516 (1982).
Wolfner, M. et al., "Integration of Amino Acid Biosynthesis into the Cell Cycle of *Saccharomyces cerevisiae*", *J. Mol. Biol.* 96: 273.
Wu, A. et al., "Transcription termination: Nucleotide sequence at 3' end of tryptophan operon *Escherichia coli*", *Proc. Natl. Acad. Sci. U.S.* 75: 5442 (1978).
Baldet et al (Jan. 1, 1995) Genbank Access No. L34413 Locus ATHSEACA.

*Primary Examiner*—Elizabeth F. McElwain
*Attorney, Agent, or Firm*—J. Timothy Meigs

[57] ABSTRACT

The present invention reveals that biotin biosynthesis in a plant is enhanced when the level of one or more of the enzymes in the plant biotin biosynthetic pathway is increased. Based upon this revelation methods which increase the level of one or more biotin biosynthetic enzymes in plant tissue are provided as a means for achieving enhanced levels of biotin in plant tissue. In particular, a method for enhancing biotin levels by introducing a chimeric gene capable of expressing a biotin biosynthetic enzyme into plant tissue is provided. Resulting transgenic plant tissue, including whole plants, having enhanced levels of biotin is also provided.

16 Claims, 2 Drawing Sheets

Comparison of Arabidopsis (A.t.) and E. coli (E.c.) BioB Proteins

```
A.t.   1 MMLVRSVFRSQLRPSVSGGLQSASCYSSLSAASAEAERTIREGPRNDWSR  50
                                                  :.|  |.
E.c.   1 .................................MAHRPRWTL   9

51 DEIKSVYDSPLLDLLFHGAQVHRHVHNFREVQQCTLLSIKTGGCSEDCSY 100
         .::...:::.||||||.:.||||:  : |:|| :||||||||:|.|||.|
      10 SQVTELFEKPLLDLLFEAQQVHRQHFDPRQVQVSTLLSIKTGACPEDCKY  59

101 CPQSSRYSTGVKAQRLMSKDAVIDAAKKAKEAGSTRFCMGAAWRDTIGRK 150
         |||.|||.||:.|:|||. :.|::.|:|||.||||||||||||::. :|.
      60 CPQTSRYKTGLEAERLMEVEQVLESARKAKAAGSTRFCMGAAWKNPHERD 109

151 TNFSQILEYIKEIRGMGMEVCCTLGMIEKQQALELKKAGLTAYNHNLDTS 200
           :  :   :..::::||:|.| ||| :.. ||  | .|||. ||||||||
     110 MPYLEQM..VQGVKAMGLEACMTLGTLSESQAQRLANAGLDYYNHNLDTS 157

201 REYYPNVITTRSYDDRLETLSHVRDAGINVCSGGIIGLGEAEEDRIGLLH 250
         .|:|.|:||||.|::||:||..||||||.||||||:||||. .|| |||
     158 PEFYGNIITTRTYQERLDTLEKVRDAGIKVCSGGIVGLGETVKDRAGLLL 207

251 TLATLPSHPESVPINALLAVKGTPLEDQKPVEIWEMIRMIGTARIVMPKA 300
         ||.||..|||||||  |: ||||||.|...|: :::|| |:.|||:||..
     208 QLANLPTPPESVPINMLVKVKGTPLADNDDVDAFDFIRTIAVARIMMPTS 257

301 MVRLSAGRVRFSMSEQALCFLAGANSIFTGEKLLTTPNNDFDADQLMFKT 350
         |||||| .:. .||:||:|||||||| |||||||| : | |  :|:..
     258 YVRLSAGREQMNEQTQAMCFMAGANSIFYGCKLLTTPNPEEDKDLQLFRK 307

351 LGLIPKPPSFSGDDSESENCEKVASASH*........... 379
         ||| |.....::|.| :. .|  ..
     308 LGLNPQQTAVLAGDNEQQQRLEQALMTPDTDEYYNAAAL* 347
```

Figure 2

ENHANCED BIOTIN BIOSYNTHESIS IN PLANT TISSUE

This is a Continuation-In-Part of U.S. patent application Ser. No. 08/351,970, filed Dec. 8, 1994, now abandoned.

FIELD OF THE INVENTION

The invention relates generally to methods for enhancing the nutritional value of plants as a food source for humans and animals. In particular, the invention relates to the application of genetic engineering techniques to achieve enhanced biotin production in plants and plant tissue.

BACKGROUND OF THE INVENTION

I. Biotin Biosynthesis

Biotin (vitamin H) is an essential nutrient for all living organisms (Eisenberg, M. A., *Adv. Enzymol.* 38: 317–372 (1973)). It is a basic component of cell metabolism which acts as a cofactor that binds covalently to carboxylases to facilitate the transfer of carboxyl groups during enzymatic carboxylation, decarboxylation and transcarboxylation reactions (Knowles, J. R., *Ann. Rev. BioChem.* 58: 195–221 (1989)). The chemical structure of the naturally occurring d-isomer of biotin is as follows:

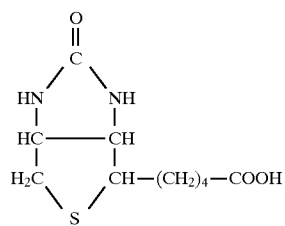

Biotin biosynthesis has been extensively studied in microorganisms, primarily through the isolation and characterization of biotin auxotrophic mutants (Eisenberg, supra). Through this work four enzymatic steps common to *E. coli* and other microorganisms for the biosynthesis of biotin from the precursor pimeloyl-CoA have been elucidated (Eisenberg, supra; Pai, C. H., *Canad. J. Microbiol* 15: 21–26 (1969); del Campillo-Campbell et al., *J. Bacteriol.* 94: 2065–2066 (1967)). Analysis of two classes of *E. coli* mutants, those defective in either the bioC (SEQ ID NO: 11) or the bioH gene, suggests that the products of these genes play a role in biotin synthesis, but at steps prior to pimeloyl-CoA. The final common steps of the biotin biosynthetic pathway are as follows:

Enzymatic steps in the biosynthesis of biotin

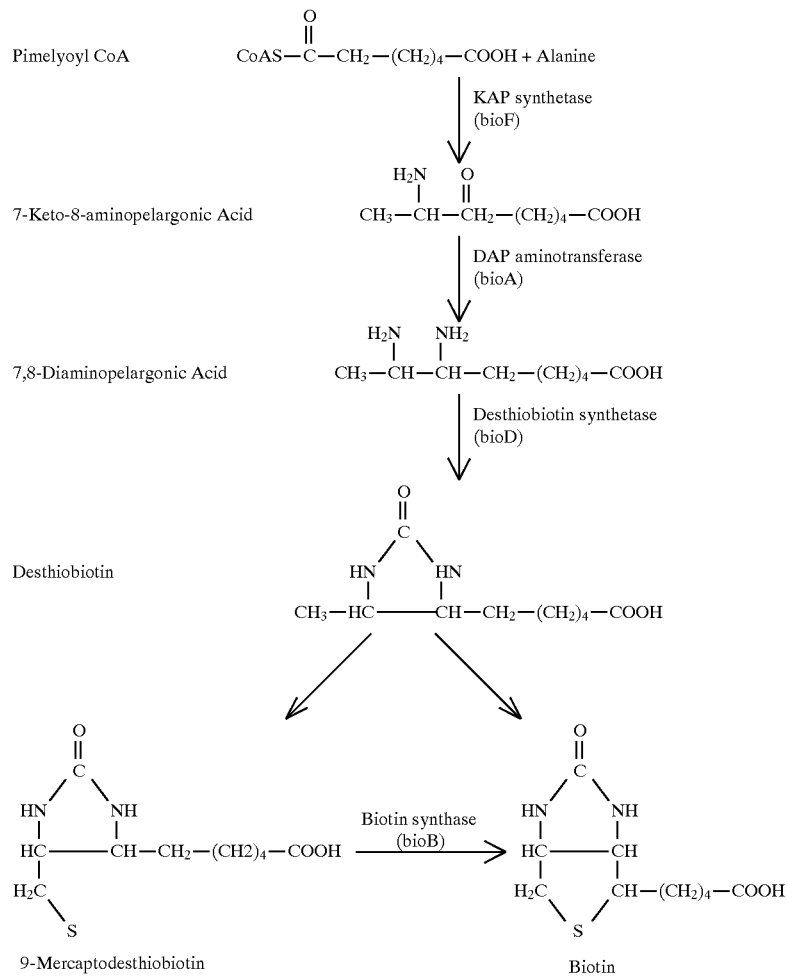

The first step in this common biotin biosynthetic pathway is the synthesis of 7-keto-8-aminopelargonic Acid (KAP) from pimeloyl-CoA and L-alanine. This step is catalyzed by an enzyme known as KAP synthetase which is encoded by the bioF gene in *E. coli* (Eisenberg, supra). This gene is part of the *E. coli* biotin operon which has been cloned and sequenced (Otsuka, A. J. et al., *J. Biol. Chem.* 263: 19577–19585 (1988); Genbank accession no. J04423).

The second step in this common biotin biosynthetic pathway is the conversion of KAP into 7,8-Diaminopelargonic Acid (DAP). This step is catalyzed by an enzyme known as DAP aminotransferase which is encoded by the bioA gene (Eisenberg and Stoner, in *Methods in Enzomology* 62: 342–347, ed. by McCormick and Wright, pub. by Acad. Press, NY (1979); Stoner and Eisenberg, *J. Biol. Chem.* 250: 4037–4043 (1975); Stoner and Eisenberg, *J. Biol. Chem.* 250: 4029–4036 (1975); Eisenberg, supra; Eisenberg and Stoner, *J. Bacteriol.* 108: 1135–1140 (1971); Pai, C. H., *J. Bacteriol* 105: 793–800 (1971)). The bioA gene is also part of the *E. coli* biotin operon which has been cloned and sequenced (Otsuka, A. J. et al., supra.; Genbank accession no. J04423).

The third step in this common biotin biosynthetic pathway is the conversion of DAP into desthiobiotin. This step is catalyzed by an enzyme known as desthiobiotin synthetase which is encoded by the bioD gene (Eisenberg, M. A., *Ann. N.Y. Acad. Sci.* 447: 335–349 (1985); Cheeseman and Pai, *J.Bacteriol.* 104: 726–733 (1970); Eisenberg and Krell, *J. Biol. Chem.* 244: 5503–5509 (1969); Pai, C. H., *J.Bacteriol.* 99: 696–701 (1969)). The bioD gene is also part of the *E. coli* biotin operon which has been cloned and sequenced (Otsuka, A. J. et al., supra.; Genbank accession no. J04423).

The final step in this common biotin biosynthetic pathway involves the addition of sulfur to desthiobiotin and subsequent ring closure, to form biotin. These steps are catalyzed by an enzyme known as biotin synthase which is encoded by the bioB gene (Eisenberg, M. A., *Ann. N. Y. Acad. Sci.* 447: 335–349 (1985); Pai, C. H., *J.Bacteriol.* 112: 1280–1287 (1972)).

The biotin biosynthetic pathway in plant cells has also been elucidated (Baldet, P. et al., *Eur. J. BioChem* 217: 479–485 (1993)). This pathway is very similar to the pathway common to all microorganisms which is described above with two additional steps. First, the pathway in plants includes the conversion of pimelic acid to pimeloyl-CoA. This step is catalyzed by an enzyme known as pimeloyl-CoA synthetase. This step may also occur in a number of microorganisms, although it may not be common to all (Gloeckler, R. et al., *Gene* 87: 63–70 (1990); Eisenberg, M., in "*Escherichia coli* and *Salmonella typhimurium*. Cellular and Molecular Biology", pp. 544–550,ed. by Neidhardt, F. C. et al., pub. by Amer. Soc. Microbiol., NY (1987); Izumi, Y. et al., in *Methods in Enzomology* 62: 327–330,ed. by McCormick and Wright, pub. by Acad. Press, NY (1979); Izumi, Y. et al., *BioChem. Biopys. Acta* 264: 210–213 (1972)).

Secondly, the conversion of desthiobiotin to biotin involves the creation of an intermediate compound, 9-mercaptodethiobiotin (Baldet et al., supra.). This intermediate may also occur in microorganisms since conversion of desthiobiotin into biotin in these organisms is not completely understood and since this compound will support the growth of *E. coli* bioB mutants (Baldet et al, supra). The presence of this intermediate indicates that another enzyme, in addition to biotin synthase, may be involved in the conversion of desthiobiotin into biotin.

II. Biotin as a Nutrient

For higher eukaryotic organisms other than plants and some fungi, biotin is an essential vitamin which must be part of the diet. Biotin deficiencies in animals can have a number of adverse effects, including a reduction in growth rate, alopecia (hair loss), scaly dermatitis, and edema and erythema of the feet (*Nutritional Reviews* 48: 352–355 (1990); Kopinski, J. S. et al., *J. Nutrition* 62: 751–759 (1989); *Poultry Science* 67: 590–595 (1988); Marshall, M. W., *Nutrition Today* 22–23: 26–29 (1987)). In humans, biotin deficiency has also been associated with a number of genetic and acquired diseases (Marshall, M. W., supra).

In general, plant-based feeds do not contain enough biotin to serve as a sufficient dietary source of this vitamin. This is especially true for stockyard animals such as pigs and chickens(Frigg, M., *Poultry Science* 63: 750–753 (1983). Enhanced performance has been observed in a number of production animals following biotin supplementation of the normal diet (Kopinski, J. S. et al. *British Journal of Nutrition* 62:751–789)). As a result, additional biotin is incorporated as a feed supplement into the diet of many animals (Robel, E. J., *poultry Science* 70: 1716–1722 (1991)).

If biotin production in plants could be increased, the need for additional biotin in animal and human diets from sources other than plants could be reduced or eliminated. Unfortunately however, not enough is known about this pathway in plants, or its regulation, to achieve the objective of increasing biotin production in plants.

One approach for enhancing biotin production which might be considered is to alter the levels of intermediates or enzymes in the biotin biosynthetic pathway. However, this approach would not be expected to work since metabolic pathways are typically tightly regulated so that metabolite synthesis remains stable despite fluctuations that may occur in the levels of available pathway intermediates and enzymes. Regulation of metabolite synthesis may involve a variety of mechanisms. Classic examples of mechanisms used to regulate metabolite synthesis in microorganisms include catabolite repression and enzyme induction (Dickson et al. *Science* 187:27–35 (1975)), feedback inhibition (Stryer, L., "BioChemistry", 2nd ed., pub. by W. H. Freeman and Co., San Francisco, pp. 500–503 (1981)), attenuation (Wu, A. and Platt, T. *Proc. Nat. Acad. Sci.* U.S. 75:5442 (1978)), and general control (M. Wolfner et al.. *J. Mol. Biol.* 15 96:273–290)). Some or all of these mechanisms may also be involved in metabolic pathway regulation in plants. Since these pathways are typically tightly regulated through a variety of mechanisms, the effect that increasing the amount of any one enzyme in a pathway will have, if any, upon the final level of the end product (metabolite) synthesized cannot be predicted.

SUMMARY OF THE INVENTION

The present invention is based upon the discovery that biotin levels in plants may be enhanced simply by increasing the levels of one or more of the enzymatic activities in the plant biotin biosynthetic pathway. The inventor has utilized this discovery to develop a general approach for increasing the levels of biotin produced in plants to enhance their nutritional value as a dietary source of biotin.

Accordingly, a method is provided for enhancing biotin levels in a plant by introducing a chimeric gene into the plant which can express an enzyme in the plant biotin biosynthetic pathway. The enzyme which may be expressed according to this aspect of the invention includes, but is not limited to, a pimeloyl-CoA synthetase, a KAP synthetase, a DAP aminotransferase, a desthiobiotin synthetase, and a biotin synthase. According to the invention the chimeric gene may encode an enzyme from a non-plant source such as a microorganism (e.g. bacteria), although an enzyme from a plant source is preferred. According to this aspect of the invention, multiple chimeric genes encoding more than one enzyme in the plant biotin biosynthetic pathway may be introduced into the plant to achieve an even greater enhancement of biotin levels.

In another aspect of the invention, transgenic plant tissue, including plants, seeds, and cultured tissue, with enhanced biotin levels is provided which comprises one or more chimeric genes expressing enzyme(s) in the plant biotin biosynthetic pathway including, but not limited to, a pimeloyl-CoA synthetase, a KAP synthetase, a DAP aininotransferase, a desthiobiotin synthetase, and a biotin synthase. This plant tissue may be lased as an improved dietary source of biotin.

Figure 1:
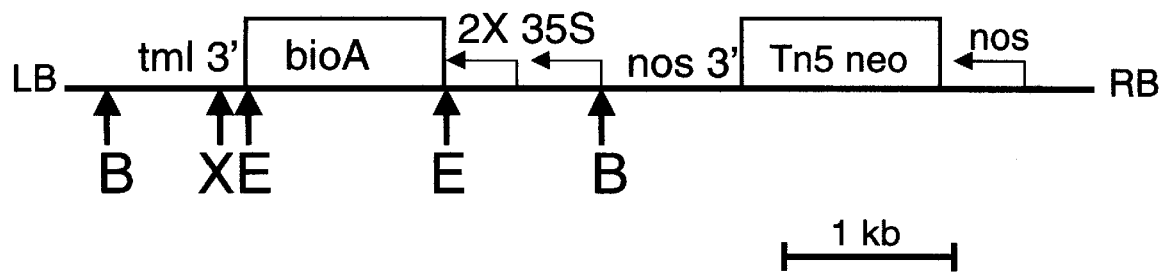
FIG. 1: T-DNA region of pCIB200/1761bioA

The E. coli bioA gene was cloned as a 1.3 kb EcoRI fragment between the double 35S promoter (2× 35S) and the tml terminater (tml 3') of pCGN1761. This 4.3 kb XbaI expression cassette was cloned into the XbaI site pCIB200.Expression of the kanamycin resistance gene (Tn5 neo) in the T-DNA portion of pCIB200 is directed by the nopaline synthase promoter (nos) and terminator (nos 3'). Direction of transcription is denoted by horizontal arrows. Restriction recognition sites XbaI (B), XhoI (X), and EcoRI (E) shown at their approximate position with vertical arrows.

FIG. 2: Comparison of the E. coli BioB protein and the protein encoded by the Arabidopsis BioB cDNA clone (NRRL #B,-21398)

This figure provides a comparison of the deduced amino acid sequence encoded by the Arabidopsis BioB cDNA (SEQ ID No: 14) and the E. coli BioB amino acid sequence (SEQ ID NO: 8).

DETAILED DESCRIPTION OF THE INVENTION

The present invention provides a general approach for enhancing biotin biosynthesis in plant tissue, thereby enhancing the nutritional value of such tissue as a dietary source of biotin. According to the present invention, the amount of biotin in plant tissue may be increased by increasing the amount of one or more biotin biosynthetic enzymes present in such tissue.

For purposes of the present invention, the term "plant tissue" is intended to include plants, seeds, progeny thereof, cultured plant cells and any other tissue of plant origin.

For purposes of the present invention, a "biotin biosynthetic enzyme" is defined as an enzyme which catalyzes one or more of the steps required for the conversion of pimelic acid into biotin in a plant. Biotin biosynthetic enzymes include, but are not necessarily limited to, a pimeloyl-CoA synthetase, a KAP synthetase, a DAP aminotransferase, a desthiobiotin synthetase, an enzyme that converts desthiobiotin to 9-mercaptodesthiobiotin, and an enzyme is that converts 9-mercaptodesthiobiotin to biotin.(these last two enzymatic conversion steps may actually be catalyzed by the same enzyme referred to as biotin synthase). Natural sources of biotin biosynthetic enzymes and the genes encoding them include plants and microbes.

The amount of a biotin biosynthetic enzyme present in a plant or plant cell may be increased using any suitable means. In particular, this may be accomplished by introducing into the plant or plant cell a chimeric gene capable of expressing a biotin biosynthetic enzyme in a plant cell. Such a chimeric gene will comprise a promoter capable of regulating gene expression in a plant, operably linked to a DNA sequence which encodes a biotin biosynthetic enzyme, followed by a transcriptional terminator and polyadenylation signal.

DNA molecules encoding biotin biosynthetic enzymes from E. coli, Bacillus sphaericus, Bacillus subtilis and Serratia marcescens are generally available (see U.S. Pat. No. 5,096,823 issued Mar. 17, 1992 to Gloeckler et al.; Otsuka, A. J. et al., J. Biol. Chem., 263(36): 19577–19585 (1988); European Patent Application no. 94108998.9 published Jan. 25, 1995 as pub. no. 635,572 to Bower, S. G. et al., Sakurai, N. et al., J.Biotechi. 36: 63–73 (1994); see also genbank accession no. D17468 for the Serratia marcescens biotin operon sequence. The E. coli coding sequences and corresponding amino acid sequence for KAP synthetase is provided in SEQ ID NOS: 1 and 2, respectively. The E. coli coding sequences and corresponding amino acid sequence for DAP aminotransferase is provided in SEQ ID NOS: 3 and 4, respectively. The E. coli coding sequences and corresponding amino acid sequence for desthiobiotin synthetase is provided in SEQ ID NOS: 5 and 6, respectively. The E. coli coding sequences and corresponding amino acid sequence for biotin synthase is provided in SEQ ID NOS: 7 and 8, respectively. The E. coli coding sequences and corresponding amino acid sequence for the bioC gene is provided in SEQ ID NOS: 11 and 12, respectively. The bioC gene encodes a protein which is involved in biotin biosynthesis at a step prior to the synthesis of 7-keto-8-aminopelargonic Acid (KAP) from pimeloyl-CoA and L-alanine which is catalyzed by an enzyme known as KAP synthetase.

DNA molecules encoding biotin biosynthetic enzymes may also be isolated from any plant species desired by applying standard molecular biological techniques. One suitable approach that has been successfully used to isolate a variety of biosynthetic genes in other metabolic pathways from higher eukaryotes is the complementation of microbial mutants deficient in the activity of interest (see, e.g. U.S. patent application Ser. no. 08/061,644 to Ward et al., incorporated by reference herein in its entirety (histidine biosynthetic genes); Frisch et al., Mol. Gen. Genet. 228: 287 (1991) (lysine biosynthetic genes); Aimi et al., J. Biol. Chem. 265: 9011 (1990)(purine biosynthetic genes); and Niyogi et al., Plant Cell 5: 1011 (1993) (tryptophan biosynthetic genes)). For this approach, a library of cDNAs from a plant of interest is cloned in a vector that can direct expression of the cDNA in the microbial host. The vector is then transformed or otherwise introduced into a microbe deficient in the activity of interest, and colonies are selected that are phenotypically no longer mutant. Suitable microbial host organisms which are deficient in the various biotin biosynthetic enzymatic activities are readily available in the art for use in this method (del Campillo-Campbell et al., J.Bacteriol. 94: 2065–2066 (1967); Pai C. H. Canad. J. Micriobiol. 15: 21–26 (1969); Cleary and Campbell, J. Bacteriol. 112: 830–839 (1972)).

Alternatively, plant or other microbial coding sequences for biotin biosynthetic enzymes may be isolated according to well known techniques based on their sequence homology to the known microbial biotin biosynthetic coding sequences. In these techniques all or part of a known biotin biosynthetic coding sequence is used as a probe which selectively hybridizes to corresponding biotin biosynthetic coding sequences present in population of cloned genomic DNA fragments or cDNA fragments (i.e. genomic or cDNA libraries) from the chosen plant. Such techniques include hybridization screening of plated DNA libraries (either plaques or colonies; see, e.g. Sambrook et al., *Molecular Cloning*, eds., Cold Spring Harbor Laboratory Press. (1989)) and amplification by PCR using oligonucleotide primers corresponding to sequence domains conserved among known amino acid sequences of the particular biotin biosynthetic enzymes (see, e.g. Innis et al.,. *PCR Protocols a Guide to Methods and Applications* eds., Academic Press (1990)).

Coding sequences for biotin biosynthetic enzymes may be genetically engineered for optimal expression in a particular crop plant. Methods for modifying coding sequences to achieve optimal expression in a particular crop species are well known (see, e.g. Perlak et al., *Proc. Natl. Acad. Sci. USA* 88: 3324 (1991); Koziel et al., *Bio/technol.* 11: 194 (1993)).

A DNA sequence coding for a biotin biosynthetic enzyme may be inserted into an expression cassette designed for plants to construct a chimeric gene according to the invention using standard genetic engineering techniques. The choice of specific regulatory sequences such as promoter, signal sequence, 5' and 3' untranslated sequences, and enhancer appropriate for the achieving the desired pattern and level of expression in the chosen plant host is within the level of skill of the routineer in the art. The resultant molecule, containing the individual elements linked in proper reading frame, may be inserted into a vector capable of being transformed into a host plant cell.

Examples of promoters capable of functioning in plants or plant cells (i.e., those capable of driving expression of associated coding sequences such as those coding for biotin biosynthetic enzymes in plant cells) include the cauliflower mosaic virus (CaMV) 19S or 35S promoters and CaMV double promoters; nopaline synthase promoters; pathogenesis-related (PR) protein promoters; small subunit of ribulose bisphosphate carboxylase (ssuRUBISCO) promoters, and the like. Preferred are the rice actin promoter (McElroy el al., *Mol. Gen. Genet.* 231: 150 (1991)), maize ubiquitin promoter (EP 0 342 926; Taylor et al., *Plant Cell Rep.* 12: 491 (1993)), and the PR-1 promoter from tobacco, Arabidopsis, or maize (see U.S. patent application Ser. No. 08/181,271 to Ryals et al., incorporated by reference herein in its entirety). Also preferred are the 35S promoter and an enhanced or double 35S promoter such as that described in Kay et al., *Science* 236: 1299–1302 (1987) and the double 35S promoter cloned into pCGN2113, deposited as ATCC 40587, which are disclosed in each of commonly owned copending application Ser. No. 07/580,431,filed Sep. 7, 1990, which is a continuation-in-part of Ser. No. 07/425, 504, filed Oct. 20, 1989, which is a continuation-in-part of Ser. No. 07/368,672, filed Jun. 20, 1989, which is a continuation-in-part of Ser. No. 07/329,018, filed Mar. 24, 1989, the relevant disclosures of which are herein incorporated by reference in their entirety. The promoters themselves may be modified to manipulate promoter strength to increase expression of the associated coding sequence in accordance with art-recognized procedures. Preferred promoters for use with the present invention will be those which confer high level constitutive expression or, more preferably, those which confer specific high level expression in the tissues incorporated into the diet of animals or humans.

Signal or transit peptides may be fused to the BBE coding sequence in the chimeric DNA constructs of the invention to direct transport of the expressed BBE to the desired site of action. Examples of signal peptides include those natively linked to the plant pathogenesis-related proteins, e.g. PR-1, PR-2, and the like. See, e.g., Payne et al., *Plant Mol. Biol.* 11:89–94 (1988). Examples of transit peptides include the chloroplast transit peptides such as those described in Von Heijne et al., *Plant Mol. Biol. Rep.* 9:104–126(1991); Mazur et al., *Plant Physiol.* 85: 1110 (1987); Vorst et al., *Gene* 65: 59 (1988), and mitochondrial transit peptides such as those described in Boutry et al., *Nature* 328:340–342 (1987). Also included are sequences that result in localization of the encoded protein to various cellular compartments such as the vacuole. See, for example, Neuhaus et al., *Proc. Natl. Acad. Sci. USA* 88: 10362–10366 (1991) and Chrispeels, *Ann. Rev. Plant Physiol. Plant Mol. Biol.* 42: 21–53 (1991 ). The relevant disclosures of these publications are incorporated herein by reference in their entirety.

The chimeric DNA construct(s) of the invention may contain multiple copies of a promoter or multiple copies of the coding sequence for a biotin biosynthetic enzyme. In addition, the construct(s) may include coding sequences for markers and coding sequences for other peptides such as signal or transit peptides, each in proper reading frame with the other functional elements in the DNA molecule. The preparation of such constructs are within the ordinary level of skill in the art.

Useful markers include peptides providing herbicide, antibiotic or drug resistance, such as, for example, resistance to hygromycin, kanamycin, G418, gentamycin, lincomycin, methotrexate, glyphosate, phosphinothricin, or the like. These markers can be used to select cells transformed with the chimeric DNA constructs of the invention from untransformed cells. Other useful markers are peptidic enzymes which can be easily detected by a visible reaction, for example a color reaction, for example luciferase, β-glucuronidase, or β-galactosidase.

Chimeric genes designed for plant expression such as those described herein can be introduced into the plant cell in a number of art-recognized ways. Those skilled in the art will appreciate that the choice of method might depend on the type of plant (i.e. monocot or dicot) and/or organelle (i.e. nucleus, chloroplast, mitochondria) targeted for transformation. Suitable methods of transforming plant cells include microinjection (Crossway et al., *BioTechniques* 4:320–334 (1986)), electroporation (Riggs et al, *Proc. Natl. Acad. Sci. USA* 83:5602–5606 (1986), Agrobacterium mediated transformation (Hinchee et al, *Biotechnology* 6:915–921 (1988)), direct gene transfer (Paszkowski et al., *EMBO J.* 3:2717–2722 (1984)), and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., *Biotechnology* 6:923–926 (1988)).see also, Weissinger et al., *Annual Rev. Genet.* 22:421–477 (1988); Sanford et al., *Particulate Science and Technology* 5:27–37 (1987)(onion); Christou et al., *Plant Physiol.* 87:671–674 (1988)(soybean); McCabe et al., *Bio/Technology* 6:923–926 (1988)(soybean); Datta et al., *Bio/Technology* 8:736–740 (1990)(rice); Klein et al., *Proc. Natl. Acad. Sci. USA*, 85:4305–4309 (1988) (maize); Klein et al., *Bio/Technology* 6:559–563 (1988) (maize); Klein et al., *Plant Physiol.* 91:440–444 (1988) (maize); Fromm et al., *Bio/Technology* 8:833–839 (1990); and Gordon-Kamm et al., *Plant Cell* 2:603–618 (1990) (maize); Svab et al., *Proc. Natl. Acad. Sci. USA* 87:8526–8530 (1990)(tobacco chloroplasts); Gordon-Kamm et al, in "Transgenic Plants", vol. 2., pp.21–33, pub. by Academic Press (1993)(maize).

Once a chimeric gene encoding a biotin biosynthetic enzyme has been transformed into a particular plant species, it may be propagated in that species or moved into other varieties of the same species, particularly including commercial varieties, using traditional breeding techniques. Alternatively, the coding sequence for a biotin biosynthetic enzyme may be isolated, genetically engineered for optimal expression and then transformed into the desired variety.

The present invention is further directed to transgenic plant tissue, including plants, seeds, and cultured tissue, stably transformed with at least one chimeric gene capable of expressing a biotin biosynthetic enzyme in the plant tissue. Expression of such a chimeric gene results in an increase in the level of the encoded biotin biosynthetic enzyme Transgenic plant tissue of the invention contains enhanced levels of biotin resulting from the expression of the chimeric gene or chimeric genes contained therein which encode one or more biotin biosynthetic enzymes. The statement "enhanced levels of biotin" is intended to mean levels of biotin greater than that found in corresponding non-transgenic plant tissue which does not contain a chimeric gene capable of expressing a biotin biosynthetic enzyme in the plant tissue.

Representative plants of the invention include any plants which may be incorporated into an animal or human diet. Preferred are agronomically important animal or human food crops such as tobacco, soya, rape, sugar beet, maize, rice, wheat, barley, oats, rye, sorghum, millet, turf, forage and the like.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by T. Maniatis, E. F. Fritsch and J. Sambrook, *Molecular Cloning: A Laboratory manual*, Cold Spring Harbor laboratory, Cold Spring Harbor, N.Y. (1982) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Example 1

Enhanced Biotin Biosynthesis in Plants Transformed with a Chimeric Gene Encoding a Biotin Biosynthetic Enzyme Generally, the *E. coli* bioA gene was expressed in tissues of the Arabidopsis bio1 auxotroph which lacks the ability to make its own biotin. Previous BioChemical evidence suggested that the bio1 mutant of Arabidopsis was defective in the DAP aminotransferase enzyme encoded by the bioA gene. Tissues from the resulting transgenic plants expressing the bioA gene not only grew in the absence of biotin, but surprisingly contained increased levels of biotin relative to non-transformed control plants. These results indicate that the level of biotin in plant tissues can be increased by expressing a chimeric gene which encodes a biotin biosynthetic enzyme. The specific details for this example are given bellow.

The bioA gene from *E. coli* strain K 12 (SEQ ID NO: 3) was amplified with ApliTaq DNA polymerase using the standard PCR protocol (Perkin Elmer). The employed oligonucleotide primers were:

(forward)
G G A A T T C A G A A G A C G A C A T G A C A A C G - GACGATCTTGCCTTTGAC (SEQ ID NO: 9)
and
(reverse)
G G A A T T C A G G T A C C A T T T A T T G - GCAAAAAAATGTTTCATCCTGTAC (SEQ ID NO: 10)
with the underlined nucleotides corresponding to the 5' and 3' ends of the bioA gene, respectively. The bases which are not underlined contain the EcoRI restriction recognition site GAATTC and a spacer of 8 or 10 nucleotides. The 1376 base pair product was ligated directly into the pCRII vector using the protocol and reagents provided in the TA cloning kit (Invitrogen; San Diego, Calif.). Plasmid DNA was prepared from cells which contained the correct bioA insert using the Magic Miniprep kit (Promega; Madison Wis.), then sequenced by the chain termination method using dideoxy terminators labeled with fluorescent dyes (Applied Biosystems, Inc., Foster City, Calif.) to ensure the fidelity of the amplified and cloned product. Plasmid DNA containing the verified bioA sequence was digested with EcoRI (Promega; Madison, Wis.) to release the 1.3 kb bioA insert, then purified on 1% Sea Plaque agarose (FMC, Rockland, Me). The EcoRI fragment was then ligated into the EcoRI site of pCGN1761,a plant expression cassette with the double 35S promoter (Kay et al., *Science* 236: 1299–1302 (1987)) and tml 3' terminator flanking the EcoRI site. This ligation mixture was transformed by electroporation (Life Technologies; Gaithersburg, Md.) into XL-1 Blue electrocompetant cells (Stratagene; LaJolla, Calif.).

Plasmids which contained the bioA gene in the correct orientation for expression were identified by standard restriction analysis (with BamHI). The expression unit containing the double 35S promoter, the bioA coding region, and the tml 3' termination sequence, was cut out of the pCGN 1761 vector with XbaI, which recognizes restriction sites which occur just outside of the desired region. The 4.9 kb XbaI fragment was then ligated into the XbaI site in the T-DNA portion of the binary plasmid pCIB200.The resulting plasmid, pCIB200/1761bioA (see FIG. 1) was transferred to *Agrobacterium tumefaciens* strain c58 GV3101 (Bechtold et al. *C.R Acad. Sci. Paris, Sciences* de la vie 316: 1194–1199 (1993)) by electroporation using standard procedures. Agrobacterium cells which contained the pCIB 200/1761bioA binary vector were used to transform biotin-supplemented homozygous bio1/bio1 Arabidopsis plants using the vacuum infiltration method (Bechtold et al., supra).

To select for stable transformants, seeds from the infiltrated plants were plated on biotin-free media which contained Kanamycin. One kanamycin-resistant plant which grew in the absence of biotin (bio1/A) was transferred to soil and assayed for total biotin production using the standard microbiological assay system (Scheiner, J. et al., *J. Agric. Food Chem.* 23: 1157–1162 (1975)) with dehydrated biotin assay medium (Difco; Detroit, Mich.). Leaf tissue from control Col-0 plants contained 18.1 pg total biotin per mg fresh weight, while leaves of the same age from the bio1/A plant produced 38.2 pg biotin per mg fresh weight. This represents a two-fold increase in total biotin produced in the mutant tissue expressing the *E. coli* bioA gene, relative to non-transformed control plants. Additionally, kanamycin-resistant $T_2$ progeny from the bio1/A plant contained elevated levels of biotin as expected.

Example 2

Isolation of Additional Biotin Biosynthetic Enzyme (BBE) Genes Based on Sequence Homology to Known BBE Coding Sequences A phage or plasmid library is plated at a density of approximately 10,000 plaques on a 10 cm Petri dish, and filter lifts of the plaques are made after overnight growth of the plates at 37° C. The plaque lifts are probed with one of the cDNAs set forth in SEQ ID NOS: 1, 3, 5, 7 and 11, labeled with 32P-dCTP by the random priming method by means of a PrimeTime kit (International Biotechnologies, Inc., New Haven, Conn.). Hybridization conditions are 7% sodium dodecyl sulfate (SDS), 0.5 M NaPO4 pH 7.0, 1 mM EDTA at 50° C. After hybridization overnight, the filters are washed with 2× SSC, 1% SDS. Positively hybridizing plaques are detected by autoradiography. After purification to single plaques, cDNA inserts are isolated, and their sequences determined by the chain termination method using dideoxy terminators labeled with fluorescent dyes (Applied Biosystems, Inc., Foster City, Calif.).

The standard experimental protocol described above can be used by one of skill in the art to obtain BBE genes sequentially homologous to the known BBE coding sequences from any other eukaryote, particularly other higher plant species.

Example 3

Isolation of Plant Biotin Biosynthetic Genes Through Functional Complementation of Bacterial Auxotrophic Mutants In general, auxotrophic mutants of E. coli which are deficient in one of the biotin biosynthetic enzymes are transformed with a library expressed plant genes (cDNA's). The plant genes are cloned en mass into a phagemid vector which can drive expression of plant cDNA's in bacteria. The transformed bacteria are then grown under selective conditions in the absence of biotin. Colonies which grow under these conditions should have the ability to synthesize their own biotin because the plant cDNA is providing the function which is missing in the original E. coli mutant.

Specifically, E. coli mutants are available for each step in the biotin biosynthetic pathway. These mutants are obtained from the E. coli Genetic Stock Center (New Haven, Conn.). The bacteria are rendered electrocompetent using standard techniques and frozen at −70° C. until transformation.

The general scheme for generating a plasmid library of expressed plant genes is to first construct a standard cDNA library in lambda phage, then perform an in vivo excision reaction on the entire library and plate at low density to obtain single colonies. The E. coli colonies are eluted off the surface of the plates, pelleted, then used to prepare plasmid DNA. In this case each colony which grows following the excision reaction represents a single cDNA from the original phage-born library. An alternative strategy would be to obtain a previously constructed cDNA library from either a DNA stock center (such as the Arabidopsis Stock Center, Columbus, Ohio), commercial sources (Stratagene, LaJolla, Calif.), or an academic colleague. Specific details for constructing a cDNA library in a suitable vector such as pBluescript are given in the package insert sent along with the kit (Stratagene, LaJolla, Calif). This plasmid carries the IPTG-inducible lacZ promoter oriented to drive expression of the inserted plant cDNA's.

Approximately 100 ng of plasmid DNA isolated from the cDNA library is used to electroporate the competent E. coli mutant cells (thawed on ice) using standard settings (1.7 Kvolts per cm for 10 milliseconds at 200 OHMS resistance and 25 µFD capacitance) on a Gene-Pulser® electroporator (Bio-Rad Laboratories, Melville, N.Y.) and a cuvette with 0.1 cm electrode gap. The electroporated cells are resuspended in 1 mL SOC (Life Technologies, Gaithersburg, Md.) and incubated at 37° C. for 1 hour with vigorous agitation (200 rpm on a rotary shaker). The cells are pelleted in a clinical centrifuge at maximum speed for 5 minutes at room temperature. The cell pellet is resuspended in 5 mLs of Vogel-Bonner E-minimal media (Vogel, H. J. and D. M. Bonner, J. Biol. Chem. 218:97–106 (1956)) to wash away excess biotin. The pelleting and washing steps are repeated two more times with the final pellet being resuspended in 1 mL minimal media. Aliquots of 100 µL are spread onto 1.5% agar plates with minimal media containing ampicillin (to select for the plasmid), IPTG (to induce the promoter driving expression of the plant gene), and any nutrients, other than biotin, which the E. coli strain requires for growth (i.e. thiamine). The plates are incubated at 37° C. for 2 to 3 days until colonies form. Plasmid DNA is isolated from 1 mL overnight cultures started by inoculating LB medium with single colonies picked with sterile toothpicks. Plasmids are retested for high-efficiency biotin complementation by retransforming the E. coli auxotroph as described. Inserts from plasmids that complement at high frequency are then sequenced and can be used as a probe on Southern and northern blots to verify copy number of the gene, and to characterize expression patterns in the plant.

Example 4

Construction of Plant Transformation Vectors

Numerous transformation vectors are available for plant transformation, and genes encoding biotin biosynthetic enzymes can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene which confers resistance to kanamycin and related antibiotics (Messing & Vierra, Gene 19: 259–268 (1982); Bevan et al., Nature 304:184–187 (1983)), the bar gene which confers resistance to the herbicide phosphinothricin (White et al., Nucl Acids Res 18: 1062 (1990), Spencer et al. Theor Appl Genet 79: 625–631(1990)), the hph gene which confers resistance to the antibiotic hygromycin (Blochinger & Diggelmann, Mol Cell Biol 4: 2929–2931), and the dhfr gene, which confers resistance to methotrexate (Bourouis et al., EMBO J. 2(7): 1099–1104(1983)).

(1) Construction of Vectors Suitable for Agrobacterium Transformation

Many vectors are available for transformation using Agrobacterium tumefaciens. These typically carry at least one T-DNA border sequence and include vectors such as pBIN19 (Bevan, Nucl. Acids Res. (1984)) and pXYZ. Below the construction of two typical vectors is described.

Construction of pCIB200 and pCIB2001

The binary vectors pCIB200 and pCIB2001 are used for the construction of recombinant vectors for use with Agrobacterium and was constructed in the following manner. pTJS75kan was created by Narn digestion of pTJS75 (Schmidhauser & Helinski, J Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982); Bevan et al., Nature 304: 184–187 (1983); McBride et al., Plant Molecular Biology 14: 266–276 (1990) ). XhoI linkers were ligated to the EcoRV fragment of pCIB7 which contains the left and right T-DNA borders, a plant selectable nos/nptII chimeric gene and the pUC polylinker (Rothstein et al., Gene 53: 153–161 (1987)), and the XhoI-digested fragment was cloned into SalI-digested pTJS75kan to create pCIB200 (see also example 19 of EP 0 332 104). pCIB200 contains the following unique polylinker restriction sites: EcoRI, SstI, KpnI, BglII, XbaI, and SalI. pCIB2001 is a derivative of pCIB200 which created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001,in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2.The pCIB2001 polylinker is suitable for the cloning of plant expression cassettes containing their own regulatory signals.

Construction of pCIB 10 and Hygromycin Selection Derivatives thereof

The binary vector pCIB 10 contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al., *Gene* 53: 153–161 (1987). Various derivatives of pCIB 10 have been constructed which incorporate the gene for hygromycin B phosphotransferase described by Gritz et al., *Gene* 25: 179–188 (1983)). These derivatives enable selection of transgenic plant cells on hygromycin only (pCIB743), or hygromycin and kanamycin (pCIB715, pCIB717).

(2) Construction of Vectors Suitable for non-Agrobacterium Transformation.

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on Agrobacterium include transformation via particle bombardment, protoplast uptake (e.g. PEG and electroporation) and microinjection. The choice of vector depends largely on the preferred selection for the species being transformed. Below, the construction of some typical vectors is described.

Construction of pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to, the *E. coli* GUS gene and the CaMV 35S transcriptional terminator and is described in the PCT published application WO 93/07278. The 35S promoter of this vector contains two ATG sequences 5' of the start site. These sites were mutated using standard PCR techniques in such a way as to remove the ATGs and generate the restriction sites Sspl and PvuII. The new restriction sites were 96 and 37 bp away from the unique SalI site and 101 and 42 bp away from the actual start site. The resultant derivative of pCIB246 was designated pCIB3025. The GUS gene was then excised from pCIB3025 by digestion with SalI and SacI, the termini rendered blunt and religated to generate plasmid pCIB3060. The plasmid pJIT82 was obtained from the John Innes Centre, Norwich and the a 400 bp SmaI fragment containing the bar gene from *Streptomyces viridochromogenes* was excised and inserted into the HpaI site of pCIB3060 (Thompson et al. EMBO J 6: 2519–2523 (1987)). This generated pCIB3064 which comprises the bar gene under the control of the CaMV 35S promoter and terminator for herbicide selection, a gene from ampicillin resistance (for selection in *E. coli*) and a polylinker with the unique sites SphI, PstI, HindIII, and BamHI. This vector is suitable for the cloning of plant expression cassettes containing their own regulatory signals.

Construction of pSOGI9 and pSOG35 pSOG35 is a transformation vector which utilizes the *E. coli* gene dihydrofolate reductase (DHFR) as a selectable marker conferring resistance to methotrexate. PCR was used to amplify the 35S promoter (~800 bp), intron 6 from the maize Adh1 gene (~550 bp) and 18 bp of the GUS untranslated leader sequence from pSOG10. A 250 bp fragment encoding the *E. coli* dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Repilacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences.

Example 5

Construction of Plant Expression Cassettes

Gene sequences intended for expression in transgenic plants are firstly assembled in expression cassettes behind a suitable promoter and upstream of a suitable transcription terminator. These expression cassettes can then be easily transferred to the plant transformation vectors described above in Example 4.

Promoter Selection

The selection of a promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and this selection will reflect the desired location of expression of the transgene. Alternatively, the selected promoter may drive expression of the gene under a light-induced or other temporally regulated promoter. A further alternative is that the selected promoter be chemically regulated. This would provide the possibility of inducing expression of the transgene only when desired and caused by treatment with a chemical inducer.

Transcriptional Terminators

A variety of transcriptional terminators are available for use in expression cassettes. These are responsible for the termination of transcription beyond the transgene and its correct polyadenylation. Appropriate transcriptional terminators and those which are known to function in plants and include the CaMV 35S terminator, the tml terminator, the nopaline synthase terminator, the pea rbcS E9 terminator. These can be used in both monocotyledons and dicotyledons.

Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adhl gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1: 1183–1200 (1987)). In the same experimental system, the intron from the maize bronze1 gene had a similar effect in enhancing expression (Callis et al., supra). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 5: 8693–8711 (1987); Skuzeski et al. *Plant Molec. Biol.* 15: 65–79 (1990))

Targeting of the Gene Product Within the Cell

Various mechanisms for targeting gene products are known to exist in plants and the sequences controlling the functioning of these mechanisms have been characterized in some detail. These mechanisms generally utilize identified transit peptides or internal amino acid sequences which have been found to target associated proteins to various cellular compartments such as the chloroplast, the mitochondrion, the peroxisome, the nucleus, the ER, the apoplast, and the vacuole.

Chloroplast Targeting

The targeting of gene products to the chloroplast is controlled by a signal sequence found at the amino terminal end of various proteins and which is c(leaved during chloroplast import yielding the mature protein (e.g. Comai et al., *J. Biol. Chem.* 263: 15104–15109 (1988)). These signal sequences can be fused to heterologous gene products to effect the import of heterologous products into the chloroplast (van den Broeck et al. *Nature* 313: 358–363 (1985)). DNA encoding for appropriate signal sequences can be isolated from the 5$\propto$ end of the cDNAs encoding the RUBISCO protein, the CAB protein, the EPSP synthase enzyme, the GS2 protein and many other proteins which are known to be chloroplast localized.

Chen & Jagendorf (*J. Biol. Chem.* 268: 2363–2367 (1993)) have described the successful use of a chloroplast transit peptide for import of a heterologous transgene. This peptide used is the transit peptide from the rbcS gene from *Nicotiana plumbaginifolia* (Poulsen et al. *Mol. Gen. Genet.* 205: 193–200 (1986)). Using the restriction enzymes DraI and SphI, or Tsp509I and SphI the DNA sequence encoding this transit peptide can be excised from plasmid prbcS-8B (Poulsen et al. supra) and manipulated for use with any of the constructions described above. The Dral-SphI fragment extends from −58 relative to the initiating rbcS ATG to, and including, the first amino acid (also a methionine) of the mature peptide immediately after the import cleavage site, whereas the Tsp509I-Sphl fragment extends from −8 relative to the initiating rbcS ATG to, and including, the first amino acid of the mature peptide. Thus, these fragment can be appropriately inserted into the polylinker of any chosen expression cassette generating a transcriptional fusion to the untranslated leader of the chosen promoter (e.g. 35S, PR-1a, actin, ubiquitin etc.), whilst enabling the insertion of a BBE gene in correct fusion downstream of the transit peptide.

Constructions of this kind are routine in the art. For example, whereas the DraI end is already blunt, the 5' Tsp509I site may be rendered blunt by T4 polymerase treatment, or may alternatively be ligated to a linker or adaptor sequence to facilitate its fusion to the chosen promoter. The 3' SphI site may be maintained as such, or may alternatively be ligated to adaptor of linker sequences to facilitate its insertion into the chosen vector in such a way as to make available appropriate restriction sites for the subsequent insertion of a selected APS gene. Ideally the ATG of the SphI site is maintained and comprises the first ATG of the selected APS gene. Chen & Jagendorf (supra) provide consensus sequences for ideal cleavage for chloroplast import, and in each case a methionine is preferred at the first position of the mature protein. At subsequent positions there is more variation and the amino acid may not be so critical. In any case, fusion constructions can be assessed for efficiency of import in vitro using the methods described by Bartlett et al. (In: Edelmann et al (Eds.) Methods in Chloroplast Molecular Biology, Elsevier. pp 1081–1091 (1982)) and Wasmann et al. (*Mol. Gen. Genet.* 205: 446–453 (1986)). Typically the best approach may be to generate fusions using the selected BBE: gene with no modifications at the aminoterminus, and only to incorporate modifications when it is apparent that such fusions are not chloroplast imported at high efficiency, in which case modifications may be made in accordance with the established literature (Chen & Jagendorf, supra; Wasman et al., supra; Ko & Ko, *J.Biol. Chem.* 267: 13910–13916 (1992)).

Targeting to Other Plant Cellular Compartments

Other gene products are localized to oorganelles such as the mitochondrion and the peroxisome (e.g. Unger et al. *Plant Molec. Biol.* 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting to cellular protein bodies has been described by Rogers et al., *Proc. Natl. Acad. Sci. USA* 82: 6512–6516 (1985)).

In addition sequences have been characterized which cause the targeting of gene products to other cell compartments. Amino terminal sequences are responsible for targeting to the ER, the apoplast, and extracellular secretion from aleurone cells (Koehler & Ho, *Plant Cell* 2: 769–783 (1990) ). Additionally, amino terminal sequences in conjunction with carboxy terminal sequences are responsible for vacuolar targeting of gene products (Shinshi et al., *Plant Molec. Biol.* 14: 357–368 (1990)).

Transgene Targeting

By the fusion of the appropriate targeting sequences described above to transgene sequences of interest it is possible to direct the transgene product to any organelle or cell compartment. For chloroplast targeting, for example, the chloroplast signal sequence from the Arabidopsis BioB gene (see Example 8), the RUBISCO gene, the CAB gene, the EPSP synthase gene, or the GS2 gene is fused in frame to the amino terminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) *Methods in Chloroplast Molecular Biology*, Elsevier. pp 1081–1091 (1982); Wasmann et al. *Mol. Gen. Genet.* 205: 446–453 (1986)). These construction techniques are well known in the art and are equally applicable to mitochondria and peroxisomes. The choice of targeting which may be required for expression of the transgenes will depend on the cellular localization of the precursor required as the starting point for a given pathway. This will usually be cytosolic or chloroplastic, although it may is some cases be mitochondrial or peroxisomal. The products of transgene expression will not normally require targeting to the ER, the apoplast or the vacuole.

The above described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

Example 6

Transformation of Dicotyledons

Transformation techniques for dicotyledons are well known in the art and include Agrobacterium-based techniques and techniques which do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., *EMBO J* 3: 2717–2722 (1984), Potrykus et al., *Mol. Gen. Genet.* 199: 169–177 (1985), Reich et al., *Biotechnology* 4: 1001–1004 (1986), and Klein et al., *Nature* 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. The many crop species which are routinely transformable by Agrobacterium include tobacco, tomato, sunflower, cotton, oilseed rape, potato, soybean, alfalfa and poplar (EP 0 317 511 (cotton), EP 0 249 432 (tomato, to Calgene), WO 87/07299 (Brassica, to Calgene), U.S. Pat. No. 4,795,855 (poplar)). Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. *Plant Cell* 5: 159–169 (1993)). The transfer of the recombinant binary vector to Agrobacterium is accomplished by a triparental mating procedure using *E. coli* carrying the recombinant binary vector, a helper *E. coli* strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, *Nucl. Acids Res.* 16: 9877(1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Example 7

Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. *Biotechnology* 4: 1093–1096 (1986)).

Patent Applications EP 0 292 435 (to Ciba-Geigy), EP 0 392 225 (to Ciba-Geigy) and WO 93/07278 (to Ciba-Geigy) describe techniques for the preparation of callus and protoplasts from an elite inbred line of maize, transformation of protoplasts using PEG or electroporation, and the regeneration of maize plants from transformed protoplasts. Gordon-Kamm et al., *Plant Cell* 2: 603–618 (1990)) and From et al., *Biotechnology* 8: 833–839 (1990)) have published techniques for transformation of A188-derived maize line using particle bombardment. Furthermore, application WO 93/07278 (to Ciba-Geigy) and Koziel et al., *Biotechnology* 11: 194–200 (1993)) describe techniques for the transformation of elite inbred lines of maize by particle bombardment. This technique utilizes immature marriage embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., *Plant Cell Rep* 7: 379–384 (1988); Shimamoto et al. *Nature* 338: 274–277 (1989); Datta et al. *Biotechnology* 8: 736–740 (1990)). Both types are also routinely transformable using particle bombardment (Christou et al. *Biotechnology* 9: 957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation was been described by Vasil et al., *Biotechnology* 10: 667–674 (1992)) using particle bombardment into cells of type C long-term regenerable callus, and also by Vasil et al., *Biotechnology* 11: 1553–1558 (1993)) and Weeks et al., *Plant Physiol.* 102: 1077–1084 (1993) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashige & Skoog,

*Physiologia Plantarum* 15: 473–497 (1962)) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics' helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent. Patent application 08/147,161 describes methods for wheat transformation and is hereby incorporated by reference.

Example 8

Isolation of an Arabidopsis Biotin Biosynthetic Gene (BioB Homologue) Based on Sequence Homology to an Expressed Sequence Tag (EST)

This example describes the isolation of a full length cDNA clone from Arabidopsis which encodes the homologue of the BioB protein from bacteria and yeast. The BioB protein plays an enzymatic role in the conversion of desthiobiotin to biotin. The precise nature of this reaction is not well understood in any organism, but apparently involves the formation of the intermediate 9-mercaptodesthiobiotin.
The EST Database The method used to isolate this clone was based upon homology to an EST (expressed sequence tag). An EST is a randomly isolated and partially sequenced cDNA clone of an expressed gene derived from a pool of mRNA isolated from an organism Since an EST is generated at random from an mRNA population and with only limited sequence information available, it cannot typically be associated with a particular function or activity based upon its mode of isolation. However, an EST may be associated with a particular function or activity based on sequence homology to genes with known function.

To date, over 14,000 EST clones from Arabidopsis have been generated and sequenced. These clones represent a portion of the total number of expressed Arabidopsis genes. For each EST approximately 300 base pairs of gene sequence from each end of these clones has been translated in all 6 possible reading frames and compared by BLAST homology searches (S. F. Altschul, et. al., *J.Mol. Biol.* 215: 403–410 (1990)) to all known protein sequences in the Genbank database. Periodically a list of the EST clones which have been generated is published in an electronic database called AATDB (an *Arabidopsis thaliana* data base) which includes identifying information for the EST (clone name, Genbank accession #, DNA sequence) and a list of protein sequences identified from the aforementioned BLAST search which have the strongest homology to the translated EST sequence. A stock of these clones are maintained in *E. coli* at The Ohio State University (Columbus, Ohio) for public distribution.
Isolation of the Full Length BioB Homologue from Arabidopsis An EST clone designated 86E12 (genbank accession # T20529) was reported as having homology to the *E. coli* BioB protein in the AATDB. This partial cDNA clone was obtained from the Arabidopsis stock center at Ohio State University center and confirmed by sequence analysis to be the same as listed as 86E12 in the AATDB. The 800 base pair insert from 86E12 was isolated and purified using standard molecular biology techniques. Using this insert as a probe, a 1.1 kb transcript was detected on a northern blot of RNA isolated from Arabidopsis leaves, indicating that 86E12 was not a full length clone. A single band was detected on Southern blots of total Arabidopsis DNA using the 86E12 insert as a probe, suggesting that the gene in the Arabidopsis genome corresponding to 86E12 was a single copy.

The 800 bp insert fragment from 86E12 was then used as a probe to isolate a full length clone from an Arabidopsis cDNA library. Approximately 250,000 plaques were screeend using the labelled 800 bp insert from 86E12. Three clones that hybridized to the labelled insert were purified to homogeneity and compared by standard restriction analysis. All three clones were similar in composition except that one clone was missing the Xho I cloning site at the 3' terminus. The two remaining clones appeared to be identical, one of which (pMP101) was sequenced completely then deposited as an *E. coli* cell stock on Feb. 6, 1995 in the Agricultural Research Service Culture Collection (NRRL #B-21398) in Peoria, Ill. The DNA sequence of the insert from this clone is set forth in SEQ ID No: 13. The amino acid sequence of the protein encoded by this cDNA is set forth in SEQ ID No: 14.

A comparison of the deduced protein sequence encoded by this gene and the *E. coli* BioB protein revealed over 50% identity and over 60% homology over the entire length of the two polypeptides (see FIG. 2). Considering the evolutionary divergence between plants and bacteria, this level of homology is remarkable and is compelling evidence that the cloned plant cDNA encodes a protein which is the functional homologue of the *E. coli* BioB protein.

Another interesting feature of this comparison is the number of excess amino acid residues on the amino terminus of the plant BioB homologue. This stretch of excess amino acids has characteristics typical of chloroplast transit peptides, indicating that this protein and other enzymes in the biotin biosynthetic pathway are probably located and active in the chloroplast in plants. Thus in order to express this gene and other BBE encoding genes in a plant to achieve enhanced biotin synthesis according to the invention, expression is preferably directed to the chloroplasts. This would not require any modification to BBE encoding genes such as the Arabidopsis gene described in this example which naturally contain a chloroplast transit peptide coding sequence. For BBE encoding genes which do not naturally contain a chloroplast transit peptide coding sequence such as the bacterial BBE encoding gene, a chloroplast transit peptide encoding sequence as described in Example 5 (see "Chloroplast Targeting section) can be added to target the BBE to the chloroplast.

Various modifications of the invention described herein will become apparent to those skilled in the art. Such modifications are intended to fall within the scope of the appended claims.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1155 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 1..1152
        ( C ) IDENTIFICATION METHOD: experimental
        ( D ) OTHER INFORMATION: /product="KAP synthetase"
                / evidence= EXPERIMENTAL ( x i ) SEQUENCE DESCRIPTION: SEQ ID NO:1:

```
ATG AGC TGG CAG GAG AAA ATC AAC GCG GCG CTC GAT GCG CGG CGT GCT        48
Met Ser Trp Gln Glu Lys Ile Asn Ala Ala Leu Asp Ala Arg Arg Ala
 1               5                  10                  15

GCC GAT GCC CTG CGT CGC CGT TAT CCG GTG GCG CAA GGA GCC GGA CGC        96
Ala Asp Ala Leu Arg Arg Arg Tyr Pro Val Ala Gln Gly Ala Gly Arg
                20                  25                  30

TGG CTG GTG GCG GAT GAT CGC CAG TAT CTG AAC TTT TCC AGT AAC GAT       144
Trp Leu Val Ala Asp Asp Arg Gln Tyr Leu Asn Phe Ser Ser Asn Asp
            35                  40                  45

TAT TTA GGT TTA AGC CAT CAT CCG CAA ATT ATC CGT GCC TGG CAG CAG       192
Tyr Leu Gly Leu Ser His His Pro Gln Ile Ile Arg Ala Trp Gln Gln
        50                  55                  60

GGG GCG GAG CAA TTT GGC ATC GGT AGC GGC GGC TCC GGT CAC GTC AGC       240
Gly Ala Glu Gln Phe Gly Ile Gly Ser Gly Gly Ser Gly His Val Ser
 65                  70                  75                  80

GGT TAT AGC GTG GTG CAT CAG GCA CTG GAA GAA GAG CTG GCC GAG TGG       288
Gly Tyr Ser Val Val His Gln Ala Leu Glu Glu Glu Leu Ala Glu Trp
                85                  90                  95

CTT GGC TAT TCG CGG GCA CTG CTG TTT ATC TCT GGT TTC GCC GCT AAT       336
Leu Gly Tyr Ser Arg Ala Leu Leu Phe Ile Ser Gly Phe Ala Ala Asn
               100                 105                 110

CAG GCA GTT ATT GCC GCG ATG ATG GCG AAA GAG GAC CGT ATT GCT GCC       384
Gln Ala Val Ile Ala Ala Met Met Ala Lys Glu Asp Arg Ile Ala Ala
           115                 120                 125

GAC CGG CTT AGC CAT GCC TCA TTG CTG GAA GCT GCC AGT TTA AGC CCG       432
Asp Arg Leu Ser His Ala Ser Leu Leu Glu Ala Ala Ser Leu Ser Pro
       130                 135                 140

TCG CAG CTT CGC CGT TTT GCT CAT AAC GAT GTC ACT CAT TTG GCG CGA       480
Ser Gln Leu Arg Arg Phe Ala His Asn Asp Val Thr His Leu Ala Arg
145                 150                 155                 160

TTG CTT GCT TCC CCC TGT CCG GGG CAG CAA ATG GTG GTG ACA GAA GGC       528
Leu Leu Ala Ser Pro Cys Pro Gly Gln Gln Met Val Val Thr Glu Gly
                165                 170                 175

GTG TTC AGC ATG GAC GGC GAT AGT GCG CCA CTG GCG GAA ATC CAG CAG       576
Val Phe Ser Met Asp Gly Asp Ser Ala Pro Leu Ala Glu Ile Gln Gln
            180                 185                 190

GTA ACG CAA CAG CAC AAT GGC TGG TTG ATG GTC GAT GAT GCC CAC GGC       624
Val Thr Gln Gln His Asn Gly Trp Leu Met Val Asp Asp Ala His Gly
        195                 200                 205
```

-continued

| | | | | | | | | | | | | | | | |
|---|---|---|---|---|---|---|---|---|---|---|---|---|---|---|---|
| ACG | GGC | GTT | ATC | GGG | GAG | CAG | GGG | CGC | GGC | AGC | TGC | TGG | CTG | CAA | AAG | 672
| Thr | Gly | Val | Ile | Gly | Glu | Gln | Gly | Arg | Gly | Ser | Cys | Trp | Leu | Gln | Lys |
| | 210 | | | | 215 | | | | | 220 | | | | | |
| GTA | AAA | CCA | GAA | TTG | CTG | GTA | GTG | ACT | TTT | GGC | AAA | GGA | TTT | GGC | GTC | 720
| Val | Lys | Pro | Glu | Leu | Leu | Val | Val | Thr | Phe | Gly | Lys | Gly | Phe | Gly | Val |
| 225 | | | | | 230 | | | | | 235 | | | | | 240 |
| AGC | GGG | GCA | GCG | GTG | CTT | TGC | TCC | AGT | ACG | GTG | GCG | GAT | TAT | CTG | CTG | 768
| Ser | Gly | Ala | Ala | Val | Leu | Cys | Ser | Ser | Thr | Val | Ala | Asp | Tyr | Leu | Leu |
| | | | | 245 | | | | | 250 | | | | | 255 | |
| CAA | TTC | GCC | CGC | CAC | CTT | ATC | TAC | AGC | ACC | AGT | ATG | CCG | CCC | GCT | CAG | 816
| Gln | Phe | Ala | Arg | His | Leu | Ile | Tyr | Ser | Thr | Ser | Met | Pro | Pro | Ala | Gln |
| | | | 260 | | | | | 265 | | | | | 270 | | |
| GCG | CAG | GCA | TTA | CGT | GCG | TCG | CTG | GCG | GTC | ATT | CGC | AGT | GAT | GAG | GGT | 864
| Ala | Gln | Ala | Leu | Arg | Ala | Ser | Leu | Ala | Val | Ile | Arg | Ser | Asp | Glu | Gly |
| | | 275 | | | | | 280 | | | | | 285 | | | |
| GAT | GCA | CGG | CGC | GAA | AAA | CTG | GCG | GCA | CTC | ATT | ACG | CGT | TTT | CGT | GCC | 912
| Asp | Ala | Arg | Arg | Glu | Lys | Leu | Ala | Ala | Leu | Ile | Thr | Arg | Phe | Arg | Ala |
| | 290 | | | | | 295 | | | | | 300 | | | | |
| GGA | GTA | CAG | GAT | TTG | CCG | TTT | ACG | CTT | GCT | GAT | TCA | TGC | AGC | GCC | ATC | 960
| Gly | Val | Gln | Asp | Leu | Pro | Phe | Thr | Leu | Ala | Asp | Ser | Cys | Ser | Ala | Ile |
| 305 | | | | | 310 | | | | | 315 | | | | | 320 |
| CAG | CCA | TTG | ATT | GTC | GGT | GAT | AAC | AGC | CGT | GCG | TTA | CAA | CTG | GCA | GAA | 1008
| Gln | Pro | Leu | Ile | Val | Gly | Asp | Asn | Ser | Arg | Ala | Leu | Gln | Leu | Ala | Glu |
| | | | | 325 | | | | | 330 | | | | | 335 | |
| AAA | CTG | CGT | CAG | CAA | GGC | TGC | TGG | GTC | ACG | GCG | ATT | CGC | CCG | CCA | ACC | 1056
| Lys | Leu | Arg | Gln | Gln | Gly | Cys | Trp | Val | Thr | Ala | Ile | Arg | Pro | Pro | Thr |
| | | | 340 | | | | | 345 | | | | | 350 | | |
| GTA | CCC | GCT | GGT | ACT | GCG | CGA | CTG | CGC | TTA | ACG | CTA | ACC | GCT | GCG | CAT | 1104
| Val | Pro | Ala | Gly | Thr | Ala | Arg | Leu | Arg | Leu | Thr | Leu | Thr | Ala | Ala | His |
| | | 355 | | | | | 360 | | | | | 365 | | | |
| GAA | ATG | CAG | GAT | ATC | GAC | CGT | CTG | CTG | GAG | GTG | CTG | CAT | GGC | AAC | GGT | 1152
| Glu | Met | Gln | Asp | Ile | Asp | Arg | Leu | Leu | Glu | Val | Leu | His | Gly | Asn | Gly |
| | 370 | | | | | 375 | | | | | 380 | | | | |
| TAA | | | | | | | | | | | | | | | | 1155

( 2 ) INFORMATION FOR SEQ ID NO:2:

( i ) SEQUENCE CHARACTERISTICS:
        ( A ) LENGTH: 384 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ser | Trp | Gln | Glu | Lys | Ile | Asn | Ala | Ala | Leu | Asp | Ala | Arg | Ala |
| 1 | | | | 5 | | | | | 10 | | | | | 15 |
| Ala | Asp | Ala | Leu | Arg | Arg | Arg | Tyr | Pro | Val | Ala | Gln | Gly | Ala | Gly | Arg
| | | | 20 | | | | | 25 | | | | | 30 | |
| Trp | Leu | Val | Ala | Asp | Asp | Arg | Gln | Tyr | Leu | Asn | Phe | Ser | Ser | Asn | Asp
| | | | 35 | | | | 40 | | | | | 45 | | |
| Tyr | Leu | Gly | Leu | Ser | His | His | Pro | Gln | Ile | Ile | Arg | Ala | Trp | Gln | Gln
| | 50 | | | | | 55 | | | | | 60 | | | |
| Gly | Ala | Glu | Gln | Phe | Gly | Ile | Gly | Ser | Gly | Ser | Gly | His | Val | Ser |
| 65 | | | | | 70 | | | | | 75 | | | | | 80 |
| Gly | Tyr | Ser | Val | Val | His | Gln | Ala | Leu | Glu | Glu | Leu | Ala | Glu | Trp |
| | | | | 85 | | | | | 90 | | | | | 95 |
| Leu | Gly | Tyr | Ser | Arg | Ala | Leu | Leu | Phe | Ile | Ser | Gly | Phe | Ala | Ala | Asn
| | | | | 100 | | | | | 105 | | | | | 110 |

| | | | | | | | | | | | | | | |
|---|---|---|---|---|---|---|---|---|---|---|---|---|---|---|
| Gln | Ala | Val<br>115 | Ile | Ala | Ala | Met | Met<br>120 | Ala | Lys | Glu | Asp | Arg<br>125 | Ile | Ala | Ala |
| Asp | Arg<br>130 | Leu | Ser | His | Ala | Ser<br>135 | Leu | Leu | Glu | Ala | Ala<br>140 | Ser | Leu | Ser | Pro |
| Ser<br>145 | Gln | Leu | Arg | Arg | Phe<br>150 | Ala | His | Asn | Asp | Val<br>155 | Thr | His | Leu | Ala | Arg<br>160 |
| Leu | Leu | Ala | Ser | Pro<br>165 | Cys | Pro | Gly | Gln | Gln<br>170 | Met | Val | Val | Thr | Glu<br>175 | Gly |
| Val | Phe | Ser | Met<br>180 | Asp | Gly | Asp | Ser | Ala<br>185 | Pro | Leu | Ala | Glu | Ile<br>190 | Gln | Gln |
| Val | Thr | Gln<br>195 | Gln | His | Asn | Gly | Trp<br>200 | Leu | Met | Val | Asp | Asp<br>205 | Ala | His | Gly |
| Thr | Gly<br>210 | Val | Ile | Gly | Glu | Gln<br>215 | Gly | Arg | Gly | Ser | Cys<br>220 | Trp | Leu | Gln | Lys |
| Val<br>225 | Lys | Pro | Glu | Leu | Leu<br>230 | Val | Val | Thr | Phe | Gly<br>235 | Lys | Gly | Phe | Gly | Val<br>240 |
| Ser | Gly | Ala | Ala | Val<br>245 | Leu | Cys | Ser | Ser | Thr<br>250 | Val | Ala | Asp | Tyr | Leu<br>255 | Leu |
| Gln | Phe | Ala | Arg<br>260 | His | Leu | Ile | Tyr | Ser<br>265 | Thr | Ser | Met | Pro | Pro<br>270 | Ala | Gln |
| Ala | Gln | Ala<br>275 | Leu | Arg | Ala | Ser | Leu<br>280 | Ala | Val | Ile | Arg | Ser<br>285 | Asp | Glu | Gly |
| Asp | Ala<br>290 | Arg | Arg | Glu | Lys | Leu<br>295 | Ala | Ala | Leu | Ile | Thr<br>300 | Arg | Phe | Arg | Ala |
| Gly<br>305 | Val | Gln | Asp | Leu | Pro<br>310 | Phe | Thr | Leu | Ala | Asp<br>315 | Ser | Cys | Ser | Ala | Ile<br>320 |
| Gln | Pro | Leu | Ile | Val<br>325 | Gly | Asp | Asn | Ser | Arg<br>330 | Ala | Leu | Gln | Leu | Ala<br>335 | Glu |
| Lys | Leu | Arg | Gln<br>340 | Gln | Gly | Cys | Trp | Val<br>345 | Thr | Ala | Ile | Arg | Pro<br>350 | Pro | Thr |
| Val | Pro | Ala<br>355 | Gly | Thr | Ala | Arg | Leu<br>360 | Arg | Leu | Thr | Leu | Thr<br>365 | Ala | Ala | His |
| Glu | Met<br>370 | Gln | Asp | Ile | Asp | Arg<br>375 | Leu | Leu | Glu | Val | Leu<br>380 | His | Gly | Asn | Gly |

( 2 ) INFORMATION FOR SEQ ID NO:3:

( i ) SEQUENCE CHARACTERISTICS:
        ( A ) LENGTH: 1296 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 1..1293
        ( C ) IDENTIFICATION METHOD: experimental
        ( D ) OTHER INFORMATION: /product="DAP aminotransferase"
                / evidence= EXPERIMENTAL ( x i ) SEQUENCE DESCRIPTION: SEQ ID NO:3:

| | | | | | | | | | | | | | | | |
|---|---|---|---|---|---|---|---|---|---|---|---|---|---|---|---|
| ATT | ATG | ACA | ACG | GAC | GAT | CTT | GCC | TTT | GAC | CAA | CGC | CAT | ATC | TGG | CAC | 48 |
| Ile | Met | Thr | Thr | Asp | Asp | Leu | Ala | Phe | Asp | Gln | Arg | His | Ile | Trp | His |
| 385 | | | | 390 | | | | | 395 | | | | | 400 |
| CCA | TAC | ACA | TCC | ATG | ACC | TCC | CCT | CTG | CCG | GTT | TAT | CCG | GTG | GTG | AGC | 96 |
| Pro | Tyr | Thr | Ser | Met | Thr | Ser | Pro | Leu | Pro | Val | Tyr | Pro | Val | Val | Ser |
| | | | | 405 | | | | | 410 | | | | | 415 |

| | | | | | | | | | | | | | | | | |
|---|---|---|---|---|---|---|---|---|---|---|---|---|---|---|---|---|
| GCC | GAA | GGT | TGC | GAG | CTG | ATT | TTG | TCT | GAC | GGC | AGA | CGC | CTG | GTT | GAC | 144 |
| Ala | Glu | Gly | Cys | Glu | Leu | Ile | Leu | Ser | Asp | Gly | Arg | Arg | Leu | Val | Asp | |
| | | 420 | | | | | | 425 | | | | | 430 | | | |
| GGT | ATG | TCG | TCC | TGG | TGG | GCG | GCG | ATC | CAC | GGC | TAC | AAT | CAC | CCG | CAG | 192 |
| Gly | Met | Ser | Ser | Trp | Trp | Ala | Ala | Ile | His | Gly | Tyr | Asn | His | Pro | Gln | |
| | | | 435 | | | | 440 | | | | | 445 | | | | |
| CTT | AAT | GCG | GCG | ATG | AAG | TCG | CAA | ATT | GAT | GCC | ATG | TCG | CAT | GTG | ATG | 240 |
| Leu | Asn | Ala | Ala | Met | Lys | Ser | Gln | Ile | Asp | Ala | Met | Ser | His | Val | Met | |
| 450 | | | | | | 455 | | | | | 460 | | | | | |
| TTT | GGC | GGT | ATC | ACC | CAT | GCG | CCA | GCC | ATT | GAG | CTG | TGC | CGC | AAA | CTG | 288 |
| Phe | Gly | Gly | Ile | Thr | His | Ala | Pro | Ala | Ile | Glu | Leu | Cys | Arg | Lys | Leu | |
| 465 | | | | | 470 | | | | | 475 | | | | | 480 | |
| GTG | GCG | ATG | AGC | GGC | CGC | AAC | GCG | CTG | GAG | TGC | GTT | TTT | CTC | GCG | GAC | 336 |
| Val | Ala | Met | Ser | Gly | Arg | Asn | Ala | Leu | Glu | Cys | Val | Phe | Leu | Ala | Asp | |
| | | | | 485 | | | | | 490 | | | | | 495 | | |
| TCC | GGT | TCC | GTA | GCG | GTG | GAA | GTG | GCG | ATG | AAA | ATG | GCG | TTG | CAG | TAC | 384 |
| Ser | Gly | Ser | Val | Ala | Val | Glu | Val | Ala | Met | Lys | Met | Ala | Leu | Gln | Tyr | |
| | | | 500 | | | | | 505 | | | | | 510 | | | |
| TGG | CAA | GCC | AAA | GGC | GAA | GCG | CGC | CAG | CGT | TTT | CTG | ACC | TTC | CGC | AAT | 432 |
| Trp | Gln | Ala | Lys | Gly | Glu | Ala | Arg | Gln | Arg | Phe | Leu | Thr | Phe | Arg | Asn | |
| | | 515 | | | | | 520 | | | | | 525 | | | | |
| GGT | TAT | CAT | GGC | GAT | ACC | TTT | GGC | GCG | ATG | TCG | GTG | TGC | GAT | CCG | GAT | 480 |
| Gly | Tyr | His | Gly | Asp | Thr | Phe | Gly | Ala | Met | Ser | Val | Cys | Asp | Pro | Asp | |
| 530 | | | | | 535 | | | | | 540 | | | | | | |
| AAC | TCA | ATG | CAC | AGT | CTG | TGG | AAA | GGC | TAC | CTG | CCA | GAA | AAC | CTG | TTT | 528 |
| Asn | Ser | Met | His | Ser | Leu | Trp | Lys | Gly | Tyr | Leu | Pro | Glu | Asn | Leu | Phe | |
| 545 | | | | | 550 | | | | | 555 | | | | | 560 | |
| GCT | CCC | GCC | CCG | CAA | AGC | CGC | ATG | GAT | GGC | GAA | TGG | GAT | GAG | CGC | GAT | 576 |
| Ala | Pro | Ala | Pro | Gln | Ser | Arg | Met | Asp | Gly | Glu | Trp | Asp | Glu | Arg | Asp | |
| | | | | 565 | | | | | 570 | | | | | 575 | | |
| ATG | GTG | GGC | TTT | GCC | CGC | CTG | ATG | GCG | GCG | CAT | CGT | CAT | GAA | ATC | GCG | 624 |
| Met | Val | Gly | Phe | Ala | Arg | Leu | Met | Ala | Ala | His | Arg | His | Glu | Ile | Ala | |
| | | | 580 | | | | | 585 | | | | | 590 | | | |
| GCG | GTG | ATC | ATT | GAG | CCG | ATT | GTC | CAG | GGC | GCA | GGC | GGG | ATG | CGC | ATG | 672 |
| Ala | Val | Ile | Ile | Glu | Pro | Ile | Val | Gln | Gly | Ala | Gly | Gly | Met | Arg | Met | |
| | | | 595 | | | | | 600 | | | | | 605 | | | |
| TAC | CAT | CCG | GAA | TGG | TTA | AAA | CGA | ATC | CGC | AAA | ATA | TGC | GAT | CGC | GAA | 720 |
| Tyr | His | Pro | Glu | Trp | Leu | Lys | Arg | Ile | Arg | Lys | Ile | Cys | Asp | Arg | Glu | |
| | 610 | | | | | 615 | | | | | 620 | | | | | |
| GGT | ATC | TTG | CTG | ATT | GCC | GAC | GAG | ATC | GCC | ACT | GGA | TTT | GGT | CGT | ACC | 768 |
| Gly | Ile | Leu | Leu | Ile | Ala | Asp | Glu | Ile | Ala | Thr | Gly | Phe | Gly | Arg | Thr | |
| 625 | | | | | 630 | | | | | 635 | | | | | 640 | |
| GGG | AAA | CTG | TTT | GCC | TGT | GAA | CAT | GCA | GAA | ATC | GCG | CCG | GAC | ATT | TTG | 816 |
| Gly | Lys | Leu | Phe | Ala | Cys | Glu | His | Ala | Glu | Ile | Ala | Pro | Asp | Ile | Leu | |
| | | | | 645 | | | | | 650 | | | | | 655 | | |
| TGC | CTC | GGT | AAA | GCC | TTA | ACC | GGC | GGC | ACA | ATG | ACC | CTT | TCC | GCC | ACA | 864 |
| Cys | Leu | Gly | Lys | Ala | Leu | Thr | Gly | Gly | Thr | Met | Thr | Leu | Ser | Ala | Thr | |
| | | | 660 | | | | 665 | | | | | 670 | | | | |
| CTC | ACC | ACG | CGC | GAG | GTT | GCA | GAA | ACC | ATC | AGT | AAC | GGT | GAA | GCC | GGT | 912 |
| Leu | Thr | Thr | Arg | Glu | Val | Ala | Glu | Thr | Ile | Ser | Asn | Gly | Glu | Ala | Gly | |
| | | | 675 | | | | | 680 | | | | | 685 | | | |
| TGC | TTT | ATG | CAT | GGG | CCA | ACT | TTT | ATG | GGC | AAT | CCG | CTG | GCC | TGC | GCG | 960 |
| Cys | Phe | Met | His | Gly | Pro | Thr | Phe | Met | Gly | Asn | Pro | Leu | Ala | Cys | Ala | |
| | 690 | | | | | 695 | | | | | 700 | | | | | |
| GCA | GCA | AAC | GCC | AGC | CTG | GCG | ATT | CTC | GAA | TCT | GGC | GAC | TGG | CAG | CAA | 1008 |
| Ala | Ala | Asn | Ala | Ser | Leu | Ala | Ile | Leu | Glu | Ser | Gly | Asp | Trp | Gln | Gln | |
| 705 | | | | | 710 | | | | | 715 | | | | | 720 | |
| CAG | GTG | GCG | GAT | ATT | GAA | GTA | CAG | CTG | CGC | GAG | CAA | CTT | GCC | CCC | GCC | 1056 |
| Gln | Val | Ala | Asp | Ile | Glu | Val | Gln | Leu | Arg | Glu | Gln | Leu | Ala | Pro | Ala | |
| | | | | 725 | | | | | 730 | | | | | 735 | | |

| | | | | | | | | | | | | | | | | |
|---|---|---|---|---|---|---|---|---|---|---|---|---|---|---|---|---|
| CGT | GAT | GCC | GAA | ATG | GTT | GCC | GAT | GTG | CGC | GTA | CTG | GGG | GCC | ATT | GGC | 1104 |
| Arg | Asp | Ala | Glu<br>740 | Met | Val | Ala | Asp | Val<br>745 | Arg | Val | Leu | Gly | Ala<br>750 | Ile | Gly | |
| GTG | GTC | GAA | ACC | ACT | CAT | CCG | GTG | AAT | ATG | GCG | GCG | CTG | CAA | AAA | TTC | 1152 |
| Val | Val | Glu<br>755 | Thr | Thr | His | Pro | Val | Asn<br>760 | Met | Ala | Ala | Leu | Gln<br>765 | Lys | Phe | |
| TTT | GTC | GAA | CAG | GGT | GTC | TGG | ATC | CGG | CCT | TTT | GGC | AAA | CTG | ATT | TAC | 1200 |
| Phe | Val<br>770 | Glu | Gln | Gly | Val | Trp<br>775 | Ile | Arg | Pro | Phe | Gly<br>780 | Lys | Leu | Ile | Tyr | |
| CTG | ATG | CCG | CCC | TAT | ATT | ATT | CTC | CCG | CAA | CAG | TTG | CAG | CGT | CTG | ACC | 1248 |
| Leu | Met<br>785 | Pro | Pro | Tyr | Ile<br>790 | Ile | Leu | Pro | Gln | Gln<br>795 | Leu | Gln | Arg | Leu | Thr<br>800 | |
| GCA | GCG | GTT | AAC | CGC | GCG | GTA | CAG | GAT | GAA | ACA | TTT | TTT | TGC | CAA | | 1293 |
| Ala | Ala | Val | Asn | Arg<br>805 | Ala | Val | Gln | Asp | Glu<br>810 | Thr | Phe | Phe | Cys | Gln<br>815 | | |
| TAA | | | | | | | | | | | | | | | | 1296 |

(2) INFORMATION FOR SEQ ID NO:4:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
| Ile<br>1 | Met | Thr | Thr | Asp<br>5 | Asp | Leu | Ala | Phe | Asp<br>10 | Gln | Arg | His | Ile | Trp His<br>15 |
| Pro | Tyr | Thr | Ser<br>20 | Met | Thr | Ser | Pro | Leu<br>25 | Pro | Val | Tyr | Pro | Val<br>30 | Val Ser |
| Ala | Glu | Gly<br>35 | Cys | Glu | Leu | Ile | Leu<br>40 | Ser | Asp | Gly | Arg | Arg<br>45 | Leu | Val Asp |
| Gly | Met<br>50 | Ser | Ser | Trp | Trp | Ala<br>55 | Ala | Ile | His | Gly | Tyr<br>60 | Asn | His | Pro Gln |
| Leu<br>65 | Asn | Ala | Ala | Met | Lys<br>70 | Ser | Gln | Ile | Asp | Ala<br>75 | Met | Ser | His | Val Met<br>80 |
| Phe | Gly | Gly | Ile | Thr<br>85 | His | Ala | Pro | Ala | Ile<br>90 | Glu | Leu | Cys | Arg | Lys Leu<br>95 |
| Val | Ala | Met | Ser<br>100 | Gly | Arg | Asn | Ala | Leu<br>105 | Glu | Cys | Val | Phe | Leu<br>110 | Ala Asp |
| Ser | Gly | Ser<br>115 | Val | Ala | Val | Glu | Val<br>120 | Ala | Met | Lys | Met | Ala<br>125 | Leu | Gln Tyr |
| Trp | Gln<br>130 | Ala | Lys | Gly | Glu | Ala<br>135 | Arg | Gln | Arg | Phe | Leu<br>140 | Thr | Phe | Arg Asn |
| Gly<br>145 | Tyr | His | Gly | Asp | Thr<br>150 | Phe | Gly | Ala | Met | Ser<br>155 | Val | Cys | Asp | Pro Asp<br>160 |
| Asn | Ser | Met | His | Ser<br>165 | Leu | Trp | Lys | Gly | Tyr<br>170 | Leu | Pro | Glu | Asn | Leu Phe<br>175 |
| Ala | Pro | Ala | Pro<br>180 | Gln | Ser | Arg | Met | Asp<br>185 | Gly | Glu | Trp | Asp | Glu<br>190 | Arg Asp |
| Met | Val | Gly<br>195 | Phe | Ala | Arg | Leu | Met<br>200 | Ala | Ala | His | Arg | His<br>205 | Glu | Ile Ala |
| Ala | Val<br>210 | Ile | Ile | Glu | Pro | Ile<br>215 | Val | Gln | Gly | Ala | Gly<br>220 | Gly | Met | Arg Met |
| Tyr<br>225 | His | Pro | Glu | Trp | Leu<br>230 | Lys | Arg | Ile | Arg | Lys<br>235 | Ile | Cys | Asp | Arg Glu<br>240 |

| | | | | | | | | | | | | | | |
|---|---|---|---|---|---|---|---|---|---|---|---|---|---|---|
| Gly | Ile | Leu | Leu | Ile | Ala | Asp | Glu | Ile | Ala | Thr | Gly | Phe | Gly | Arg | Thr |
| | | | | 245 | | | | | 250 | | | | | 255 | |
| Gly | Lys | Leu | Phe | Ala | Cys | Glu | His | Ala | Glu | Ile | Ala | Pro | Asp | Ile | Leu |
| | | | 260 | | | | | 265 | | | | | 270 | | |
| Cys | Leu | Gly | Lys | Ala | Leu | Thr | Gly | Thr | Met | Thr | Leu | Ser | Ala | Thr |
| | | 275 | | | | | 280 | | | | 285 | | | |
| Leu | Thr | Thr | Arg | Glu | Val | Ala | Glu | Thr | Ile | Ser | Asn | Gly | Glu | Ala | Gly |
| | 290 | | | | | 295 | | | | | 300 | | | | |
| Cys | Phe | Met | His | Gly | Pro | Thr | Phe | Met | Gly | Asn | Pro | Leu | Ala | Cys | Ala |
| 305 | | | | | 310 | | | | | 315 | | | | | 320 |
| Ala | Ala | Asn | Ala | Ser | Leu | Ala | Ile | Leu | Glu | Ser | Gly | Asp | Trp | Gln | Gln |
| | | | | 325 | | | | | 330 | | | | | 335 | |
| Gln | Val | Ala | Asp | Ile | Glu | Val | Gln | Leu | Arg | Glu | Gln | Leu | Ala | Pro | Ala |
| | | | 340 | | | | | 345 | | | | | 350 | | |
| Arg | Asp | Ala | Glu | Met | Val | Ala | Asp | Val | Arg | Val | Leu | Gly | Ala | Ile | Gly |
| | | 355 | | | | | 360 | | | | | 365 | | | |
| Val | Val | Glu | Thr | Thr | His | Pro | Val | Asn | Met | Ala | Ala | Leu | Gln | Lys | Phe |
| | 370 | | | | | 375 | | | | | 380 | | | | |
| Phe | Val | Glu | Gln | Gly | Val | Trp | Ile | Arg | Pro | Phe | Gly | Lys | Leu | Ile | Tyr |
| 385 | | | | | 390 | | | | | 395 | | | | | 400 |
| Leu | Met | Pro | Pro | Tyr | Ile | Ile | Leu | Pro | Gln | Gln | Leu | Gln | Arg | Leu | Thr |
| | | | | 405 | | | | | 410 | | | | | 415 | |
| Ala | Ala | Val | Asn | Arg | Ala | Val | Gln | Asp | Glu | Thr | Phe | Phe | Cys | Gln |
| | | | 420 | | | | | 425 | | | | | 430 | | |

(2) INFORMATION FOR SEQ ID NO:5:

(i) SEQUENCE CHARACTERISTICS:
        (A) LENGTH: 660 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION: 1..657
        (C) IDENTIFICATION METHOD: experimental
        (D) OTHER INFORMATION: /product="desthiobiotin
            synthetase"
        / evidence= EXPERIMENTAL (xi) SEQUENCE DESCRIPTION: SEQ ID NO:5:

| | | | | | | | | | | | | | | | |
|---|---|---|---|---|---|---|---|---|---|---|---|---|---|---|---|
| GTG | AGT | AAA | CGT | TAT | TTT | GTC | ACC | GGA | ACG | GAT | ACC | GAA | GTG | GGG | AAA | 48 |
| Val | Ser | Lys | Arg | Tyr | Phe | Val | Thr | Gly | Thr | Asp | Thr | Glu | Val | Gly | Lys |
| | | | 435 | | | | | 440 | | | | | 445 | | |
| ACT | GTC | GCC | AGT | TGT | GCA | CTT | TTA | CAA | GCC | GCA | AAG | CGA | GCA | GGC | TAC | 96 |
| Thr | Val | Ala | Ser | Cys | Ala | Leu | Leu | Gln | Ala | Ala | Lys | Arg | Ala | Gly | Tyr |
| | | | 450 | | | | | 455 | | | | | 460 | | |
| CGG | ACG | GCA | GGT | TAT | AAA | CCG | GTC | GCC | TCT | GGC | AGC | GAA | AAG | ACC | CCG | 144 |
| Arg | Thr | Ala | Gly | Tyr | Lys | Pro | Val | Ala | Ser | Gly | Ser | Glu | Lys | Thr | Pro |
| | | | 465 | | | | | 470 | | | | | 475 | | |
| GAA | GGT | TTA | CGC | AAT | AGC | GAC | GCG | CTG | GCG | TTA | CAG | CGC | AAC | AGC | AGC | 192 |
| Glu | Gly | Leu | Arg | Asn | Ser | Asp | Ala | Leu | Ala | Leu | Gln | Arg | Asn | Ser | Ser |
| 480 | | | | | 485 | | | | | 490 | | | | | 495 |
| CTG | CAG | CTG | GAT | TAC | GCA | ACA | GTA | AAT | CCT | TAC | ACC | TTC | GCA | GAA | CCC | 240 |
| Leu | Gln | Leu | Asp | Tyr | Ala | Thr | Val | Asn | Pro | Tyr | Thr | Phe | Ala | Glu | Pro |
| | | | | 500 | | | | | 505 | | | | | 510 | |
| ACT | TCG | CCG | CAC | ATC | ATC | AGC | GCG | CAA | GAG | GGC | AGA | CCG | ATA | GAA | TCA | 288 |

| | | | | | | | | | | | | | | | |
|---|---|---|---|---|---|---|---|---|---|---|---|---|---|---|---|
| Thr | Ser | Pro | His | Ile | Ile | Ser | Ala | Gln | Glu | Gly | Arg | Pro | Ile | Glu | Ser |
| | | | 515 | | | | | 520 | | | | | 525 | | |

| TTG | GTA | ATG | AGC | GCC | GGA | TTA | CGC | GCG | CTT | GAA | CAA | CAG | GCT | GAC | TGG | 336 |
|---|---|---|---|---|---|---|---|---|---|---|---|---|---|---|---|---|
| Leu | Val | Met | Ser | Ala | Gly | Leu | Arg | Ala | Leu | Glu | Gln | Gln | Ala | Asp | Trp | |
| | | 530 | | | | | 535 | | | | | 540 | | | | |

| GTG | TTA | GTG | GAA | GGT | GCT | GGC | GGC | TGG | TTT | ACG | CCG | CTT | TCT | GAC | ACT | 384 |
|---|---|---|---|---|---|---|---|---|---|---|---|---|---|---|---|---|
| Val | Leu | Val | Glu | Gly | Ala | Gly | Gly | Trp | Phe | Thr | Pro | Leu | Ser | Asp | Thr | |
| | 545 | | | | | 550 | | | | | 555 | | | | | |

| TTC | ACT | TTT | GCA | GAT | TGG | GTA | ACA | CAG | GAA | CAA | CTG | CCG | GTG | ATA | CTG | 432 |
|---|---|---|---|---|---|---|---|---|---|---|---|---|---|---|---|---|
| Phe | Thr | Phe | Ala | Asp | Trp | Val | Thr | Gln | Glu | Gln | Leu | Pro | Val | Ile | Leu | |
| 560 | | | | | 565 | | | | | 570 | | | | | 575 | |

| GTA | GTT | GGT | GTG | AAA | CTC | GGC | TGT | ATT | AAT | CAC | GCG | ATG | TTG | ACT | GCA | 480 |
|---|---|---|---|---|---|---|---|---|---|---|---|---|---|---|---|---|
| Val | Val | Gly | Val | Lys | Leu | Gly | Cys | Ile | Asn | His | Ala | Met | Leu | Thr | Ala | |
| | | | | 580 | | | | | 585 | | | | | 590 | | |

| CAG | GTA | ATA | CAA | CAC | GCC | GGA | CTG | ACT | CTG | GCG | GGT | TGG | GTG | GCG | AAC | 528 |
|---|---|---|---|---|---|---|---|---|---|---|---|---|---|---|---|---|
| Gln | Val | Ile | Gln | His | Ala | Gly | Leu | Thr | Leu | Ala | Gly | Trp | Val | Ala | Asn | |
| | | | 595 | | | | | 600 | | | | | 605 | | | |

| GAT | GTT | ACG | CCT | CCG | GGA | AAA | CGT | CAC | GCT | GAA | TAT | ATG | ACC | ACG | CTC | 576 |
|---|---|---|---|---|---|---|---|---|---|---|---|---|---|---|---|---|
| Asp | Val | Thr | Pro | Pro | Gly | Lys | Arg | His | Ala | Glu | Tyr | Met | Thr | Thr | Leu | |
| | | 610 | | | | | 615 | | | | | 620 | | | | |

| ACC | CGC | ATG | ATT | CCG | CGC | CGC | TGC | TGG | GAG | AGA | TCC | CCT | GGC | TTG | CAG | 624 |
|---|---|---|---|---|---|---|---|---|---|---|---|---|---|---|---|---|
| Thr | Arg | Met | Ile | Pro | Arg | Arg | Cys | Trp | Glu | Arg | Ser | Pro | Gly | Leu | Gln | |
| | 625 | | | | | 630 | | | | | 635 | | | | | |

| AAA | ATC | CAG | AAA | ATG | CGG | CAA | CCG | GAA | AGT | ACA | TAA | | | | | 660 |
|---|---|---|---|---|---|---|---|---|---|---|---|---|---|---|---|---|
| Lys | Ile | Gln | Lys | Met | Arg | Gln | Pro | Glu | Ser | Thr | | | | | | |
| 640 | | | | | 645 | | | | | 650 | | | | | | |

( 2 ) INFORMATION FOR SEQ ID NO:6:

( i ) SEQUENCE CHARACTERISTICS:
        ( A ) LENGTH: 219 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Val | Ser | Lys | Arg | Tyr | Phe | Val | Thr | Gly | Thr | Asp | Thr | Glu | Val | Gly | Lys |
|---|---|---|---|---|---|---|---|---|---|---|---|---|---|---|---|
| 1 | | | | 5 | | | | | 10 | | | | | 15 | |

| Thr | Val | Ala | Ser | Cys | Ala | Leu | Leu | Gln | Ala | Ala | Lys | Arg | Ala | Gly | Tyr |
|---|---|---|---|---|---|---|---|---|---|---|---|---|---|---|---|
| | | | 20 | | | | | 25 | | | | | 30 | | |

| Arg | Thr | Ala | Gly | Tyr | Lys | Pro | Val | Ala | Ser | Gly | Ser | Glu | Lys | Thr | Pro |
|---|---|---|---|---|---|---|---|---|---|---|---|---|---|---|---|
| | | | 35 | | | | 40 | | | | | 45 | | | |

| Glu | Gly | Leu | Arg | Asn | Ser | Asp | Ala | Leu | Ala | Leu | Gln | Arg | Asn | Ser | Ser |
|---|---|---|---|---|---|---|---|---|---|---|---|---|---|---|---|
| | 50 | | | | | 55 | | | | | 60 | | | | |

| Leu | Gln | Leu | Asp | Tyr | Ala | Thr | Val | Asn | Pro | Tyr | Thr | Phe | Ala | Glu | Pro |
|---|---|---|---|---|---|---|---|---|---|---|---|---|---|---|---|
| 65 | | | | | 70 | | | | | 75 | | | | | 80 |

| Thr | Ser | Pro | His | Ile | Ile | Ser | Ala | Gln | Glu | Gly | Arg | Pro | Ile | Glu | Ser |
|---|---|---|---|---|---|---|---|---|---|---|---|---|---|---|---|
| | | | | 85 | | | | | 90 | | | | | 95 | |

| Leu | Val | Met | Ser | Ala | Gly | Leu | Arg | Ala | Leu | Glu | Gln | Gln | Ala | Asp | Trp |
|---|---|---|---|---|---|---|---|---|---|---|---|---|---|---|---|
| | | | 100 | | | | | 105 | | | | | 110 | | |

| Val | Leu | Val | Glu | Gly | Ala | Gly | Gly | Trp | Phe | Thr | Pro | Leu | Ser | Asp | Thr |
|---|---|---|---|---|---|---|---|---|---|---|---|---|---|---|---|
| | | 115 | | | | | 120 | | | | | 125 | | | |

| Phe | Thr | Phe | Ala | Asp | Trp | Val | Thr | Gln | Glu | Gln | Leu | Pro | Val | Ile | Leu |
|---|---|---|---|---|---|---|---|---|---|---|---|---|---|---|---|
| | 130 | | | | | 135 | | | | | 140 | | | | |

| Val | Val | Gly | Val | Lys | Leu | Gly | Cys | Ile | Asn | His | Ala | Met | Leu | Thr | Ala |
|---|---|---|---|---|---|---|---|---|---|---|---|---|---|---|---|
| 145 | | | | | 150 | | | | | 155 | | | | | 160 |

| Gln | Val | Ile | Gln | His | Ala | Gly | Leu | Thr | Leu | Ala | Gly | Trp | Val | Ala | Asn |
|---|---|---|---|---|---|---|---|---|---|---|---|---|---|---|---|
| | | | | 165 | | | | | 170 | | | | | 175 | |

| Asp | Val | Thr | Pro | Pro | Gly | Lys | Arg | His | Ala | Glu | Tyr | Met | Thr | Thr | Leu |
|---|---|---|---|---|---|---|---|---|---|---|---|---|---|---|---|
|  |  |  | 180 |  |  |  |  | 185 |  |  |  |  | 190 |  |  |

| Thr | Arg | Met | Ile | Pro | Arg | Arg | Cys | Trp | Glu | Arg | Ser | Pro | Gly | Leu | Gln |
|---|---|---|---|---|---|---|---|---|---|---|---|---|---|---|---|
|  |  | 195 |  |  |  |  | 200 |  |  |  |  | 205 |  |  |  |

| Lys | Ile | Gln | Lys | Met | Arg | Gln | Pro | Glu | Ser | Thr |
|---|---|---|---|---|---|---|---|---|---|---|
|  | 210 |  |  |  |  | 215 |  |  |  |  |

( 2 ) INFORMATION FOR SEQ ID NO:7:

( i ) SEQUENCE CHARACTERISTICS:
        ( A ) LENGTH: 1041 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 1..1038
        ( C ) IDENTIFICATION METHOD: experimental
        ( D ) OTHER INFORMATION: /product="biotin synthase"
                / evidence= EXPERIMENTAL ( x i ) SEQUENCE DESCRIPTION: SEQ ID NO:7:

| ATG | GCT | CAC | CGC | CCA | CGC | TGG | ACA | TTG | TCG | CAA | GTC | ACA | GAA | TTA | TTT | 48 |
|---|---|---|---|---|---|---|---|---|---|---|---|---|---|---|---|---|
| Met | Ala | His | Arg | Pro | Arg | Trp | Thr | Leu | Ser | Gln | Val | Thr | Glu | Leu | Phe |  |
| 220 |  |  |  | 225 |  |  |  |  | 230 |  |  |  |  | 235 |  |  |

| GAA | AAA | CCG | TTG | CTG | GAT | CTG | CTG | TTT | GAA | GCG | CAG | CAG | GTG | CAT | CGC | 96 |
|---|---|---|---|---|---|---|---|---|---|---|---|---|---|---|---|---|
| Glu | Lys | Pro | Leu | Leu | Asp | Leu | Leu | Phe | Glu | Ala | Gln | Gln | Val | His | Arg |  |
|  |  |  |  | 240 |  |  |  |  | 245 |  |  |  |  | 250 |  |  |

| CAG | CAT | TTC | GAT | CCT | CGT | CAG | GTG | CAG | GTC | AGC | ACG | TTG | CTG | TCG | ATT | 144 |
|---|---|---|---|---|---|---|---|---|---|---|---|---|---|---|---|---|
| Gln | His | Phe | Asp | Pro | Arg | Gln | Val | Gln | Val | Ser | Thr | Leu | Leu | Ser | Ile |  |
|  |  |  | 255 |  |  |  |  | 260 |  |  |  |  | 265 |  |  |  |

| AAG | ACC | GGA | GCT | TGT | CCG | GAA | GAT | TGC | AAA | TAC | TGC | CCG | CAA | ACG | TCG | 192 |
|---|---|---|---|---|---|---|---|---|---|---|---|---|---|---|---|---|
| Lys | Thr | Gly | Ala | Cys | Pro | Glu | Asp | Cys | Lys | Tyr | Cys | Pro | Gln | Thr | Ser |  |
|  |  | 270 |  |  |  |  | 275 |  |  |  |  | 280 |  |  |  |  |

| CGC | TAC | AAA | ACC | GGG | CTG | GAA | GCC | GAG | CGG | TTG | ATG | GAA | GTT | GAA | CAG | 240 |
|---|---|---|---|---|---|---|---|---|---|---|---|---|---|---|---|---|
| Arg | Tyr | Lys | Thr | Gly | Leu | Glu | Ala | Glu | Arg | Leu | Met | Glu | Val | Glu | Gln |  |
|  | 285 |  |  |  |  | 290 |  |  |  |  | 295 |  |  |  |  |  |

| GTG | CTG | GAG | TCG | GCG | CGC | AAA | GCG | AAA | GCG | GCA | GGA | TCG | ACG | CGC | TTC | 288 |
|---|---|---|---|---|---|---|---|---|---|---|---|---|---|---|---|---|
| Val | Leu | Glu | Ser | Ala | Arg | Lys | Ala | Lys | Ala | Ala | Gly | Ser | Thr | Arg | Phe |  |
| 300 |  |  |  |  | 305 |  |  |  |  | 310 |  |  |  |  | 315 |  |

| TGT | ATG | GGC | GCG | GCG | TGG | AAG | AAT | CCC | CAC | GAA | CGC | GAT | ATG | CCG | TAC | 336 |
|---|---|---|---|---|---|---|---|---|---|---|---|---|---|---|---|---|
| Cys | Met | Gly | Ala | Ala | Trp | Lys | Asn | Pro | His | Glu | Arg | Asp | Met | Pro | Tyr |  |
|  |  |  |  | 320 |  |  |  |  | 325 |  |  |  |  | 330 |  |  |

| CTG | GAA | CAA | ATG | GTG | CAG | GGG | GTA | AAA | GCG | ATG | GGG | CTG | GAG | GCG | TGT | 384 |
|---|---|---|---|---|---|---|---|---|---|---|---|---|---|---|---|---|
| Leu | Glu | Gln | Met | Val | Gln | Gly | Val | Lys | Ala | Met | Gly | Leu | Glu | Ala | Cys |  |
|  |  |  | 335 |  |  |  |  | 340 |  |  |  |  | 345 |  |  |  |

| ATG | ACG | CTG | GGC | ACG | TTG | AGT | GAA | TCT | CAG | GCG | CAG | CGC | CTC | GCG | AAC | 432 |
|---|---|---|---|---|---|---|---|---|---|---|---|---|---|---|---|---|
| Met | Thr | Leu | Gly | Thr | Leu | Ser | Glu | Ser | Gln | Ala | Gln | Arg | Leu | Ala | Asn |  |
|  |  | 350 |  |  |  |  | 355 |  |  |  |  | 360 |  |  |  |  |

| GCC | GGG | CTG | GAT | TAC | TAC | AAC | CAC | AAC | CTG | GAC | ACC | TCG | CCG | GAG | TTT | 480 |
|---|---|---|---|---|---|---|---|---|---|---|---|---|---|---|---|---|
| Ala | Gly | Leu | Asp | Tyr | Tyr | Asn | His | Asn | Leu | Asp | Thr | Ser | Pro | Glu | Phe |  |
|  | 365 |  |  |  |  | 370 |  |  |  |  | 375 |  |  |  |  |  |

| TAC | GGC | AAT | ATC | ATC | ACC | ACA | CGC | ACT | TAT | CAG | GAA | CGC | CTC | GAT | ACG | 528 |
|---|---|---|---|---|---|---|---|---|---|---|---|---|---|---|---|---|
| Tyr | Gly | Asn | Ile | Ile | Thr | Thr | Arg | Thr | Tyr | Gln | Glu | Arg | Leu | Asp | Thr |  |
| 380 |  |  |  |  | 385 |  |  |  |  | 390 |  |  |  |  | 395 |  |

| CTG | GAA | AAA | GTG | CGC | GAT | GCC | GGG | ATC | AAA | GTC | TGT | TCT | GGC | GGC | ATT | 576 |
|---|---|---|---|---|---|---|---|---|---|---|---|---|---|---|---|---|
| Leu | Glu | Lys | Val | Arg | Asp | Ala | Gly | Ile | Lys | Val | Cys | Ser | Gly | Gly | Ile |  |
|  |  |  |  | 400 |  |  |  |  | 405 |  |  |  |  | 410 |  |  |

| GTG | GGC | TTA | GGC | GAA | ACG | GTA | AAA | GAT | CGC | GCC | GGA | TTA | TTG | CTG | CAA | 624 |
|---|---|---|---|---|---|---|---|---|---|---|---|---|---|---|---|---|

| | | | | | | | | | | | | | | | |
|---|---|---|---|---|---|---|---|---|---|---|---|---|---|---|---|
| Val | Gly | Leu | Gly | Glu | Thr | Val | Lys | Asp | Arg | Ala | Gly | Leu | Leu | Leu | Gln |
| | | 415 | | | | | 420 | | | | | 425 | | | |
| CTG | GCA | AAC | CTG | CCG | ACG | CCG | CCG | GAA | AGC | GTG | CCA | ATC | AAC | ATG | CTG | 672 |
| Leu | Ala | Asn | Leu | Pro | Thr | Pro | Pro | Glu | Ser | Val | Pro | Ile | Asn | Met | Leu |
| | | 430 | | | | | 435 | | | | | 440 | | | |
| GTG | AAG | GTG | AAA | GGC | ACG | CCG | CTT | GCC | GAT | AAC | GAT | GAT | GTC | GAT | GCC | 720 |
| Val | Lys | Val | Lys | Gly | Thr | Pro | Leu | Ala | Asp | Asn | Asp | Asp | Val | Asp | Ala |
| | 445 | | | | | 450 | | | | | 455 | | | | |
| TTT | GAT | TTT | ATT | CGC | ACC | ATT | GCG | GTC | GCG | CGG | ATC | ATG | ATG | CCA | ACC | 768 |
| Phe | Asp | Phe | Ile | Arg | Thr | Ile | Ala | Val | Ala | Arg | Ile | Met | Met | Pro | Thr |
| 460 | | | | | 465 | | | | | 470 | | | | | 475 |
| TCT | TAC | GTG | CGC | CTT | TCT | GCC | GGA | CGC | GAG | CAG | ATG | AAC | GAA | CAG | ACT | 816 |
| Ser | Tyr | Val | Arg | Leu | Ser | Ala | Gly | Arg | Glu | Gln | Met | Asn | Glu | Gln | Thr |
| | | | | 480 | | | | | 485 | | | | | 490 | |
| CAG | GCG | ATG | TGC | TTT | ATG | GCA | GGC | GCA | AAC | TCG | ATT | TTC | TAC | GGT | TGC | 864 |
| Gln | Ala | Met | Cys | Phe | Met | Ala | Gly | Ala | Asn | Ser | Ile | Phe | Tyr | Gly | Cys |
| | | | 495 | | | | | 500 | | | | | 505 | | |
| AAA | CTG | CTG | ACC | ACG | CCG | AAT | CCG | GAA | GAA | GAT | AAA | GAC | CTG | CAA | CTG | 912 |
| Lys | Leu | Leu | Thr | Thr | Pro | Asn | Pro | Glu | Glu | Asp | Lys | Asp | Leu | Gln | Leu |
| | | 510 | | | | | 515 | | | | | 520 | | | |
| TTC | CGC | AAA | CTG | GGG | CTA | AAT | CCG | CAG | CAA | ACT | GCC | GTG | CTG | GCA | GGG | 960 |
| Phe | Arg | Lys | Leu | Gly | Leu | Asn | Pro | Gln | Gln | Thr | Ala | Val | Leu | Ala | Gly |
| | 525 | | | | | 530 | | | | | 535 | | | | |
| GAT | AAC | GAA | CAA | CAG | CAA | CGT | CTT | GAA | CAG | GCG | CTG | ATG | ACC | CCG | GAC | 1008 |
| Asp | Asn | Glu | Gln | Gln | Gln | Arg | Leu | Glu | Gln | Ala | Leu | Met | Thr | Pro | Asp |
| 540 | | | | | 545 | | | | | 550 | | | | | 555 |
| ACC | GAC | GAA | TAT | TAC | AAC | GCG | GCA | GCA | TTA | TGA | | | | | | 1041 |
| Thr | Asp | Glu | Tyr | Tyr | Asn | Ala | Ala | Ala | Leu | | | | | | |
| | | | | 560 | | | | | 565 | | | | | | |

( 2 ) INFORMATION FOR SEQ ID NO:8:

( i ) SEQUENCE CHARACTERISTICS:
        ( A ) LENGTH: 346 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Ala | His | Arg | Pro | Arg | Trp | Thr | Leu | Ser | Gln | Val | Thr | Glu | Leu | Phe |
| 1 | | | | 5 | | | | | 10 | | | | | 15 | |
| Glu | Lys | Pro | Leu | Leu | Asp | Leu | Leu | Phe | Glu | Ala | Gln | Gln | Val | His | Arg |
| | | | | 20 | | | | | 25 | | | | | 30 | |
| Gln | His | Phe | Asp | Pro | Arg | Gln | Val | Gln | Val | Ser | Thr | Leu | Leu | Ser | Ile |
| | | | 35 | | | | | 40 | | | | | 45 | | |
| Lys | Thr | Gly | Ala | Cys | Pro | Glu | Asp | Cys | Lys | Tyr | Cys | Pro | Gln | Thr | Ser |
| | 50 | | | | | 55 | | | | | 60 | | | | |
| Arg | Tyr | Lys | Thr | Gly | Leu | Glu | Ala | Glu | Arg | Leu | Met | Glu | Val | Glu | Gln |
| 65 | | | | | 70 | | | | | 75 | | | | | 80 |
| Val | Leu | Glu | Ser | Ala | Arg | Lys | Ala | Lys | Ala | Ala | Gly | Ser | Thr | Arg | Phe |
| | | | | 85 | | | | | 90 | | | | | 95 | |
| Cys | Met | Gly | Ala | Ala | Trp | Lys | Asn | Pro | His | Glu | Arg | Asp | Met | Pro | Tyr |
| | | | | 100 | | | | | 105 | | | | | 110 | |
| Leu | Glu | Gln | Met | Val | Gln | Gly | Val | Lys | Ala | Met | Gly | Leu | Glu | Ala | Cys |
| | | | | 115 | | | | | 120 | | | | | 125 | |
| Met | Thr | Leu | Gly | Thr | Leu | Ser | Glu | Ser | Gln | Ala | Gln | Arg | Leu | Ala | Asn |
| | | 130 | | | | | 135 | | | | | 140 | | | |
| Ala | Gly | Leu | Asp | Tyr | Tyr | Asn | His | Asn | Leu | Asp | Thr | Ser | Pro | Glu | Phe |
| 145 | | | | | 150 | | | | | 155 | | | | | 160 |

| | | | | | | | | | | | | | | |
|---|---|---|---|---|---|---|---|---|---|---|---|---|---|---|
|Tyr|Gly|Asn|Ile|Ile<br>165|Thr|Thr|Arg|Thr|Tyr<br>170|Gln|Glu|Arg|Leu|Asp<br>175|Thr|
|Leu|Glu|Lys|Val<br>180|Arg|Asp|Ala|Gly|Ile<br>185|Lys|Val|Cys|Ser|Gly<br>190|Gly|Ile|
|Val|Gly|Leu<br>195|Gly|Glu|Thr|Val|Lys<br>200|Asp|Arg|Ala|Gly|Leu<br>205|Leu|Leu|Gln|
|Leu|Ala<br>210|Asn|Leu|Pro|Thr|Pro<br>215|Pro|Glu|Ser|Val|Pro<br>220|Ile|Asn|Met|Leu|
|Val<br>225|Lys|Val|Lys|Gly|Thr<br>230|Pro|Leu|Ala|Asp|Asn<br>235|Asp|Asp|Val|Asp|Ala<br>240|
|Phe|Asp|Phe|Ile|Arg<br>245|Thr|Ile|Ala|Val|Ala<br>250|Arg|Ile|Met|Met|Pro<br>255|Thr|
|Ser|Tyr|Val|Arg<br>260|Leu|Ser|Ala|Gly|Arg<br>265|Glu|Gln|Met|Asn|Glu<br>270|Gln|Thr|
|Gln|Ala|Met<br>275|Cys|Phe|Met|Ala|Gly<br>280|Ala|Asn|Ser|Ile|Phe<br>285|Tyr|Gly|Cys|
|Lys|Leu<br>290|Leu|Thr|Thr|Pro|Asn<br>295|Pro|Glu|Glu|Asp|Lys<br>300|Asp|Leu|Gln|Leu|
|Phe<br>305|Arg|Lys|Leu|Gly|Leu<br>310|Asn|Pro|Gln|Gln|Thr<br>315|Ala|Val|Leu|Ala|Gly<br>320|
|Asp|Asn|Glu|Gln|Gln<br>325|Gln|Arg|Leu|Glu|Gln<br>330|Ala|Leu|Met|Thr|Pro<br>335|Asp|
|Thr|Asp|Glu|Tyr<br>340|Tyr|Asn|Ala|Ala|Ala<br>345|Leu| | | | | | |

( 2 ) INFORMATION FOR SEQ ID NO:9:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "oligonucleotide primer for
PCR of bioA gene"

( i i i ) HYPOTHETICAL: NO ( x i ) SEQUENCE DESCRIPTION: SEQ ID NO:9:

GGAATTCAGA AGACGACATG ACAACGGACG ATCTTGCCTT TGAC    44

( 2 ) INFORMATION FOR SEQ ID NO:10:

( i ) SEQUENCE CHARACTERISTICS:
( A ) LENGTH: 46 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "oligonucleotide primer for
PCR of bioA gene"

( i i i ) HYPOTHETICAL: NO ( x i ) SEQUENCE DESCRIPTION: SEQ ID NO:10:

GGAATTCAGG TACCATTTAT TGGCAAAAAA ATGTTTCATC CTGTAC    46

( 2 ) INFORMATION FOR SEQ ID NO:11:

( i ) SEQUENCE CHARACTERISTICS:
( A ) LENGTH: 756 base pairs ( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i x ) FEATURE:
( A ) NAME/KEY: CDS
( B ) LOCATION: 1..753
( C ) IDENTIFICATION METHOD: experimental
( D ) OTHER INFORMATION: /product="bioC gene product; functions in biotin pathway before pimelic acid"
/ evidence= EXPERIMENTAL ( x i ) SEQUENCE DESCRIPTION: SEQ ID NO:11:

| ATG | GCA | ACG | GTT | AAT | AAA | CAA | GCC | ATT | GCA | GCG | GCA | TTT | GGT | CGG | GCA | 48 |
| Met | Ala | Thr | Val | Asn | Lys | Gln | Ala | Ile | Ala | Ala | Ala | Phe | Gly | Arg | Ala | |
| | | | 350 | | | | 355 | | | | | 360 | | | | |

| GCC | GCA | CAC | TAT | GAG | CAA | CAT | GCA | GAT | CTA | CAG | CGC | CAG | AGT | GCT | GAC | 96 |
| Ala | Ala | His | Tyr | Glu | Gln | His | Ala | Asp | Leu | Gln | Arg | Gln | Ser | Ala | Asp | |
| | | 365 | | | | 370 | | | | | 375 | | | | | |

| GCC | TTA | CTG | GCA | ATG | CTT | CCA | CAG | CGT | AAA | TAC | ACC | CAC | GTA | CTG | GAC | 144 |
| Ala | Leu | Leu | Ala | Met | Leu | Pro | Gln | Arg | Lys | Tyr | Thr | His | Val | Leu | Asp | |
| 380 | | | | | 385 | | | | | 390 | | | | | | |

| GCG | GGT | TGT | GGA | CCT | GGC | TGG | ATG | AGC | CGC | CAC | TGG | CGG | GAA | CGT | CAC | 192 |
| Ala | Gly | Cys | Gly | Pro | Gly | Trp | Met | Ser | Arg | His | Trp | Arg | Glu | Arg | His | |
| 395 | | | | 400 | | | | | 405 | | | | | 410 | | |

| GCG | CAG | GTG | ACG | GCC | TTA | GAT | CTC | TCG | CCG | CCA | ATG | CTT | GTT | CAG | GCA | 240 |
| Ala | Gln | Val | Thr | Ala | Leu | Asp | Leu | Ser | Pro | Pro | Met | Leu | Val | Gln | Ala | |
| | | | | 415 | | | | 420 | | | | | 425 | | | |

| CGC | CAG | AAG | GAT | GCC | GCA | GAC | CAT | TAT | CTG | GCG | GGA | GAT | ATC | GAA | TCC | 288 |
| Arg | Gln | Lys | Asp | Ala | Ala | Asp | His | Tyr | Leu | Ala | Gly | Asp | Ile | Glu | Ser | |
| | | | 430 | | | | 435 | | | | | 440 | | | | |

| CTG | CCG | TTA | GCG | ACT | GCG | ACG | TTC | GAT | CTT | GCA | TGG | AGC | AAT | CTC | GCA | 336 |
| Leu | Pro | Leu | Ala | Thr | Ala | Thr | Phe | Asp | Leu | Ala | Trp | Ser | Asn | Leu | Ala | |
| | | 445 | | | | 450 | | | | | 455 | | | | | |

| GTG | CAG | TGG | TGC | GGT | AAT | TTA | TCC | ACG | GCA | CTC | CGC | GAG | CTG | TAT | CGG | 384 |
| Val | Gln | Trp | Cys | Gly | Asn | Leu | Ser | Thr | Ala | Leu | Arg | Glu | Leu | Tyr | Arg | |
| | 460 | | | | | 465 | | | | | 470 | | | | | |

| GTG | GTG | CGC | CCC | AAA | GGC | GTG | GTC | GCG | TTT | ACC | ACG | CTG | GTG | CAG | GGA | 432 |
| Val | Val | Arg | Pro | Lys | Gly | Val | Val | Ala | Phe | Thr | Thr | Leu | Val | Gln | Gly | |
| 475 | | | | | 480 | | | | | 485 | | | | | 490 | |

| TCG | TTA | CCC | GAA | CGT | CAT | CAG | GCG | TGG | CAG | GCG | GTG | GAC | GAG | CGT | CCG | 480 |
| Ser | Leu | Pro | Glu | Arg | His | Gln | Ala | Trp | Gln | Ala | Val | Asp | Glu | Arg | Pro | |
| | | | | 495 | | | | 500 | | | | | 505 | | | |

| CAT | GCT | AAT | CGC | TTT | TTA | CCG | CCA | GAT | GAA | ATC | GAA | CAG | TCG | CTG | AAC | 528 |
| His | Ala | Asn | Arg | Phe | Leu | Pro | Pro | Asp | Glu | Ile | Glu | Gln | Ser | Leu | Asn | |
| | | | 510 | | | | 515 | | | | | 520 | | | | |

| GGC | GTG | CAT | TAT | CAA | CAT | CAT | ATT | CAG | CCC | ATC | ACG | CTG | TGG | TTT | GAT | 576 |
| Gly | Val | His | Tyr | Gln | His | His | Ile | Gln | Pro | Ile | Thr | Leu | Trp | Phe | Asp | |
| | | 525 | | | | 530 | | | | | 535 | | | | | |

| GAT | GCG | CTC | AGT | GCC | ATG | CGT | TCG | CTG | AAA | GGC | ATC | GGT | GCC | ACG | CAT | 624 |
| Asp | Ala | Leu | Ser | Ala | Met | Arg | Ser | Leu | Lys | Gly | Ile | Gly | Ala | Thr | His | |
| | 540 | | | | | 545 | | | | | 550 | | | | | |

| CTT | CAT | GAA | GGG | CGC | GAC | CCG | CGA | ATA | TTA | ACG | CGT | TCG | CAG | TTG | CAG | 672 |
| Leu | His | Glu | Gly | Arg | Asp | Pro | Arg | Ile | Leu | Thr | Arg | Ser | Gln | Leu | Gln | |
| 555 | | | | | 560 | | | | | 565 | | | | | 570 | |

| CGA | TTG | CAA | CTG | GCC | TGG | CCG | CAA | CAG | CAG | GGG | CGA | TAT | CCT | CTG | ACG | 720 |
| Arg | Leu | Gln | Leu | Ala | Trp | Pro | Gln | Gln | Gln | Gly | Arg | Tyr | Pro | Leu | Thr | |
| | | | | 575 | | | | | 580 | | | | | 585 | | |

| TAT | CAT | CTT | TTT | TTG | GGA | GTG | ATT | GCT | CGT | GAG | TAA | | | | | 756 |
| Tyr | His | Leu | Phe | Leu | Gly | Val | Ile | Ala | Arg | Glu | | | | | | |

(2) INFORMATION FOR SEQ ID NO:12:

(i) SEQUENCE CHARACTERISTICS:
    (A) LENGTH: 251 amino acids
    (B) TYPE: amino acid
    (D) TOPOLOGY: linear (ii) MOLECULE TYPE: protein (xi) SEQUENCE DESCRIPTION: SEQ ID NO:12:

| Met | Ala | Thr | Val | Asn | Lys | Gln | Ala | Ile | Ala | Ala | Phe | Gly | Arg | Ala |
|---|---|---|---|---|---|---|---|---|---|---|---|---|---|---|
| 1 | | | | 5 | | | | | 10 | | | | | 15 |

| Ala | Ala | His | Tyr | Glu | Gln | His | Ala | Asp | Leu | Gln | Arg | Gln | Ser | Ala | Asp |
|---|---|---|---|---|---|---|---|---|---|---|---|---|---|---|---|
| | | | 20 | | | | | 25 | | | | | 30 | | |

| Ala | Leu | Leu | Ala | Met | Leu | Pro | Gln | Arg | Lys | Tyr | Thr | His | Val | Leu | Asp |
|---|---|---|---|---|---|---|---|---|---|---|---|---|---|---|---|
| | | 35 | | | | | 40 | | | | | 45 | | | |

| Ala | Gly | Cys | Gly | Pro | Gly | Trp | Met | Ser | Arg | His | Trp | Arg | Glu | Arg | His |
|---|---|---|---|---|---|---|---|---|---|---|---|---|---|---|---|
| | 50 | | | | | 55 | | | | | 60 | | | | |

| Ala | Gln | Val | Thr | Ala | Leu | Asp | Leu | Ser | Pro | Pro | Met | Leu | Val | Gln | Ala |
|---|---|---|---|---|---|---|---|---|---|---|---|---|---|---|---|
| 65 | | | | | 70 | | | | | 75 | | | | | 80 |

| Arg | Gln | Lys | Asp | Ala | Ala | Asp | His | Tyr | Leu | Ala | Gly | Asp | Ile | Glu | Ser |
|---|---|---|---|---|---|---|---|---|---|---|---|---|---|---|---|
| | | | | 85 | | | | | 90 | | | | | 95 | |

| Leu | Pro | Leu | Ala | Thr | Ala | Thr | Phe | Asp | Leu | Ala | Trp | Ser | Asn | Leu | Ala |
|---|---|---|---|---|---|---|---|---|---|---|---|---|---|---|---|
| | | | 100 | | | | | 105 | | | | | 110 | | |

| Val | Gln | Trp | Cys | Gly | Asn | Leu | Ser | Thr | Ala | Leu | Arg | Glu | Leu | Tyr | Arg |
|---|---|---|---|---|---|---|---|---|---|---|---|---|---|---|---|
| | | | 115 | | | | | 120 | | | | | 125 | | |

| Val | Val | Arg | Pro | Lys | Gly | Val | Val | Ala | Phe | Thr | Thr | Leu | Val | Gln | Gly |
|---|---|---|---|---|---|---|---|---|---|---|---|---|---|---|---|
| | 130 | | | | | 135 | | | | | 140 | | | | |

| Ser | Leu | Pro | Glu | Arg | His | Gln | Ala | Trp | Gln | Ala | Val | Asp | Glu | Arg | Pro |
|---|---|---|---|---|---|---|---|---|---|---|---|---|---|---|---|
| 145 | | | | | 150 | | | | | 155 | | | | | 160 |

| His | Ala | Asn | Arg | Phe | Leu | Pro | Pro | Asp | Glu | Ile | Glu | Gln | Ser | Leu | Asn |
|---|---|---|---|---|---|---|---|---|---|---|---|---|---|---|---|
| | | | | 165 | | | | | 170 | | | | | 175 | |

| Gly | Val | His | Tyr | Gln | His | His | Ile | Gln | Pro | Ile | Thr | Leu | Trp | Phe | Asp |
|---|---|---|---|---|---|---|---|---|---|---|---|---|---|---|---|
| | | | 180 | | | | | 185 | | | | | 190 | | |

| Asp | Ala | Leu | Ser | Ala | Met | Arg | Ser | Leu | Lys | Gly | Ile | Gly | Ala | Thr | His |
|---|---|---|---|---|---|---|---|---|---|---|---|---|---|---|---|
| | | | 195 | | | | | 200 | | | | | 205 | | |

| Leu | His | Glu | Gly | Arg | Asp | Pro | Arg | Ile | Leu | Thr | Arg | Ser | Gln | Leu | Gln |
|---|---|---|---|---|---|---|---|---|---|---|---|---|---|---|---|
| | 210 | | | | | 215 | | | | | 220 | | | | |

| Arg | Leu | Gln | Leu | Ala | Trp | Pro | Gln | Gln | Gln | Gly | Arg | Tyr | Pro | Leu | Thr |
|---|---|---|---|---|---|---|---|---|---|---|---|---|---|---|---|
| 225 | | | | | 230 | | | | | 235 | | | | | 240 |

| Tyr | His | Leu | Phe | Leu | Gly | Val | Ile | Ala | Arg | Glu |
|---|---|---|---|---|---|---|---|---|---|---|
| | | | | 245 | | | | | 250 | |

(2) INFORMATION FOR SEQ ID NO:13:

(i) SEQUENCE CHARACTERISTICS:
    (A) LENGTH: 1351 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (ix) FEATURE:
    (A) NAME/KEY: CDS
    (B) LOCATION: 59..1192
    (D) OTHER INFORMATION: /product="Arabidopsis BioB enzyme"

( x i ) SEQUENCE DESCRIPTION: SEQ ID NO:13:

```
GGCACGAGCT CATTTCTTCT TCTTCTTCTT TTTCCACATT TTCTGATTAG CAGATCAA                    58

ATG ATG CTT GTT CGA TCT GTA TTT CGA TCT CAG TTG CGA CCC TCT GTC               106
Met Met Leu Val Arg Ser Val Phe Arg Ser Gln Leu Arg Pro Ser Val
 1           5                   10                  15

TCG GGT GGT CTG CAA TCT GCT TCT TGC TAT TCT TCA TTA TCT GCT GCT               154
Ser Gly Gly Leu Gln Ser Ala Ser Cys Tyr Ser Ser Leu Ser Ala Ala
             20                  25                  30

TCA GCT GAA GCT GAG AGG ACT ATC AGA GAA GGT CCC AGA AAC GAT TGG               202
Ser Ala Glu Ala Glu Arg Thr Ile Arg Glu Gly Pro Arg Asn Asp Trp
         35                  40                  45

AGT AGA GAT GAA ATC AAG TCT GTT TAT GAT TCT CCT CTT CTT GAC CTC               250
Ser Arg Asp Glu Ile Lys Ser Val Tyr Asp Ser Pro Leu Leu Asp Leu
     50                  55                  60

CTC TTC CAT GGA GCT CAG GTT CAT AGA CAT GTT CAT AAC TTC AGG GAG               298
Leu Phe His Gly Ala Gln Val His Arg His Val His Asn Phe Arg Glu
 65              70                  75                      80

GTA CAA CAA TGT ACC CTC CTC TCC ATA AAG ACT GGT GGC TGT AGT GAA               346
Val Gln Gln Cys Thr Leu Leu Ser Ile Lys Thr Gly Gly Cys Ser Glu
                 85                  90                  95

GAC TGT TCA TAT TGT CCT CAG TCT TCG AGA TAT AGC ACT GGA GTT AAG               394
Asp Cys Ser Tyr Cys Pro Gln Ser Ser Arg Tyr Ser Thr Gly Val Lys
             100                 105                 110

GCA CAA AGA CTC ATG TCT AAG GAC GCT GTC ATT GAT GCT GCT AAG AAG               442
Ala Gln Arg Leu Met Ser Lys Asp Ala Val Ile Asp Ala Ala Lys Lys
         115                 120                 125

GCA AAA GAA GCT GGG AGC ACA CGT TTT TGC ATG GGT GCT GCT TGG CGA               490
Ala Lys Glu Ala Gly Ser Thr Arg Phe Cys Met Gly Ala Ala Trp Arg
     130                 135                 140

GAT ACA ATT GGA CGG AAA ACC AAC TTC AGC CAG ATT CTT GAA TAC ATC               538
Asp Thr Ile Gly Arg Lys Thr Asn Phe Ser Gln Ile Leu Glu Tyr Ile
145                 150                 155                 160

AAA GAA ATA AGA GGC ATG GGG ATG GAA GTT TGC TGC ACC TTA GGC ATG               586
Lys Glu Ile Arg Gly Met Gly Met Glu Val Cys Cys Thr Leu Gly Met
                 165                 170                 175

ATT GAG AAA CAA CAA GCA CTA GAG CTA AAG AAG GCT GGC CTC ACT GCT               634
Ile Glu Lys Gln Gln Ala Leu Glu Leu Lys Lys Ala Gly Leu Thr Ala
             180                 185                 190

TAT AAC CAC AAT CTT GAT ACT TCA AGA GAG TAC TAC CCA AAC GTC ATC               682
Tyr Asn His Asn Leu Asp Thr Ser Arg Glu Tyr Tyr Pro Asn Val Ile
         195                 200                 205

ACT ACT AGA AGT TAT GAC GAT CGC CTT GAA ACT CTT AGC CAT GTT CGT               730
Thr Thr Arg Ser Tyr Asp Asp Arg Leu Glu Thr Leu Ser His Val Arg
     210                 215                 220

GAT GCT GGA ATC AAC GTT TGT TCA GGA GGA ATC ATA GGG CTT GGT GAG               778
Asp Ala Gly Ile Asn Val Cys Ser Gly Gly Ile Ile Gly Leu Gly Glu
225                 230                 235                 240

GCA GAG GAA GAC AGA ATA GGT TTA TTA CAC ACG CTG GCA ACA CTT CCT               826
Ala Glu Glu Asp Arg Ile Gly Leu Leu His Thr Leu Ala Thr Leu Pro
                 245                 250                 255

TCT CAC CCT GAG AGT GTT CCC ATT AAT GCT CTA CTT GCA GTG AAA GGC               874
Ser His Pro Glu Ser Val Pro Ile Asn Ala Leu Leu Ala Val Lys Gly
             260                 265                 270

ACT CCT CTT GAA GAC CAG AAG CCA GTT GAG ATA TGG GAG ATG ATC AGG               922
Thr Pro Leu Glu Asp Gln Lys Pro Val Glu Ile Trp Glu Met Ile Arg
         275                 280                 285

ATG ATT GGA ACC GCA CGT ATT GTA ATG CCA AAA GCG ATG GTG AGA CTG               970
Met Ile Gly Thr Ala Arg Ile Val Met Pro Lys Ala Met Val Arg Leu
     290                 295                 300
```

```
TCT  GCT  GGT  AGA  GTC  CGG  TTC  TCA  ATG  TCC  GAA  CAA  GCT  CTC  TGT  TTC      1018
Ser  Ala  Gly  Arg  Val  Arg  Phe  Ser  Met  Ser  Glu  Gln  Ala  Leu  Cys  Phe
305                 310                 315                           320

CTT  GCT  GGT  GCA  AAC  TCT  ATC  TTC  ACC  GGA  GAG  AAG  CTT  TTA  ACC  ACA      1066
Leu  Ala  Gly  Ala  Asn  Ser  Ile  Phe  Thr  Gly  Glu  Lys  Leu  Leu  Thr  Thr
                    325                 330                           335

CCA  AAC  AAT  GAT  TTT  GAC  GCT  GAC  CAG  CTC  ATG  TTC  AAG  ACA  TTA  GGC      1114
Pro  Asn  Asn  Asp  Phe  Asp  Ala  Asp  Gln  Leu  Met  Phe  Lys  Thr  Leu  Gly
               340                 345                           350

CTC  ATT  CCT  AAA  CCG  CCA  AGT  TTC  TCT  GGA  GAT  GAT  TCT  GAA  TCA  GAA      1162
Leu  Ile  Pro  Lys  Pro  Pro  Ser  Phe  Ser  Gly  Asp  Asp  Ser  Glu  Ser  Glu
          355                 360                           365

AAC  TGC  GAG  AAA  GTT  GCT  TCC  GCT  TCT  CAC  TAATATCATT ATCCACTTTT             1212
Asn  Cys  Glu  Lys  Val  Ala  Ser  Ala  Ser  His
370                           375

TTTTTTGTTT GGAGTCGGGA CACTATAGAG CAGTCCCTTT TACTATGTAG CATGGTTTGA                   1272
CGATTTTGTG ATATCATTTT TCGTTAATCG TTATTCGAAG ATGTCTAGAT TTCTCATCTG                   1332
AAAAAAAAAA AAAAAAAA                                                                 1351
```

( 2 ) INFORMATION FOR SEQ ID NO:14:

( i ) SEQUENCE CHARACTERISTICS:
        ( A ) LENGTH: 378 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met  Met  Leu  Val  Arg  Ser  Val  Phe  Arg  Ser  Gln  Leu  Arg  Pro  Ser  Val
1                   5                   10                            15

Ser  Gly  Gly  Leu  Gln  Ser  Ala  Ser  Cys  Tyr  Ser  Ser  Leu  Ser  Ala  Ala
               20                  25                            30

Ser  Ala  Glu  Ala  Glu  Arg  Thr  Ile  Arg  Glu  Gly  Pro  Arg  Asn  Asp  Trp
               35                  40                  45

Ser  Arg  Asp  Glu  Ile  Lys  Ser  Val  Tyr  Asp  Ser  Pro  Leu  Leu  Asp  Leu
     50                  55                       60

Leu  Phe  His  Gly  Ala  Gln  Val  His  Arg  His  Val  His  Asn  Phe  Arg  Glu
65                       70                       75                            80

Val  Gln  Gln  Cys  Thr  Leu  Leu  Ser  Ile  Lys  Thr  Gly  Gly  Cys  Ser  Glu
                    85                       90                       95

Asp  Cys  Ser  Tyr  Cys  Pro  Gln  Ser  Ser  Arg  Tyr  Ser  Thr  Gly  Val  Lys
                    100                      105                 110

Ala  Gln  Arg  Leu  Met  Ser  Lys  Asp  Ala  Val  Ile  Asp  Ala  Ala  Lys  Lys
          115                      120                      125

Ala  Lys  Glu  Ala  Gly  Ser  Thr  Arg  Phe  Cys  Met  Gly  Ala  Ala  Trp  Arg
     130                      135                      140

Asp  Thr  Ile  Gly  Arg  Lys  Thr  Asn  Phe  Ser  Gln  Ile  Leu  Glu  Tyr  Ile
145                      150                      155                           160

Lys  Glu  Ile  Arg  Gly  Met  Gly  Met  Glu  Val  Cys  Cys  Thr  Leu  Gly  Met
                         165                      170                 175

Ile  Glu  Lys  Gln  Gln  Ala  Leu  Glu  Leu  Lys  Lys  Ala  Gly  Leu  Thr  Ala
                    180                      185                 190

Tyr  Asn  His  Asn  Leu  Asp  Thr  Ser  Arg  Glu  Tyr  Tyr  Pro  Asn  Val  Ile
          195                      200                      205

Thr  Thr  Arg  Ser  Tyr  Asp  Asp  Arg  Leu  Glu  Thr  Leu  Ser  His  Val  Arg
     210                      215                      220
```

| | | | | | | | | | | | | | | |
|---|---|---|---|---|---|---|---|---|---|---|---|---|---|---|
| Asp<br>225 | Ala | Gly | Ile | Asn | Val<br>230 | Cys | Ser | Gly | Gly | Ile<br>235 | Ile | Gly | Leu | Gly | Glu<br>240 |
| Ala | Glu | Glu | Asp | Arg<br>245 | Ile | Gly | Leu | Leu | His<br>250 | Thr | Leu | Ala | Thr | Leu<br>255 | Pro |
| Ser | His | Pro | Glu<br>260 | Ser | Val | Pro | Ile | Asn<br>265 | Ala | Leu | Leu | Ala | Val<br>270 | Lys | Gly |
| Thr | Pro | Leu<br>275 | Glu | Asp | Gln | Lys | Pro<br>280 | Val | Glu | Ile | Trp | Glu<br>285 | Met | Ile | Arg |
| Met | Ile<br>290 | Gly | Thr | Ala | Arg | Ile<br>295 | Val | Met | Pro | Lys | Ala<br>300 | Met | Val | Arg | Leu |
| Ser<br>305 | Ala | Gly | Arg | Val | Arg<br>310 | Phe | Ser | Met | Ser | Glu<br>315 | Gln | Ala | Leu | Cys | Phe<br>320 |
| Leu | Ala | Gly | Ala | Asn<br>325 | Ser | Ile | Phe | Thr | Gly<br>330 | Glu | Lys | Leu | Leu | Thr<br>335 | Thr |
| Pro | Asn | Asn | Asp<br>340 | Phe | Asp | Ala | Asp | Gln<br>345 | Leu | Met | Phe | Lys | Thr<br>350 | Leu | Gly |
| Leu | Ile | Pro<br>355 | Lys | Pro | Pro | Ser | Phe<br>360 | Ser | Gly | Asp | Asp | Ser<br>365 | Glu | Ser | Glu |
| Asn | Cys<br>370 | Glu | Lys | Val | Ala | Ser<br>375 | Ala | Ser | His | | | | | | |

We claim:

1. A method for increasing the amount of biotin in a plant cell relative to the amount of biotin naturally in said plant cell, comprising increasing the amount of a DAP aminotransferase or a biotin synthase in said plant cell by transforming said plant cell with a chimeric gene capable of expressing said DAP aminotransferase or said biotin synthase.

2. Transgenic plant tissue which produces enhanced levels of biotin relative to the level of biotin naturally found in non-transgenic plant tissue, comprising a chimeric gene encoding a DAP aminotransferase or a biotin synthase, wherein said chimeric gene is capable of expressing said DAP aminotransferase or said biotin synthase in said transgenic plant tissue.

3. A transgenic plant which produces enhanced levels of biotin relative to the level of biotin naturally found in a non-transgenic plant, comprising a chimeric gene encoding a DAP aminotransferase or a biotin synthase, wherein said chimeric gene is capable of expressing said DAP aminotransferase or said biotin synthase in said transgenic plant.

4. The transgenic plant of claim 3 wherein said transgenic plant is selected from the group consisting of Arabidopsis, wheat, corn, soybean, canola, tobacco.

5. The method of claim 1 wherein said chimeric gene comprises a chloroplast transit peptide signal sequence.

6. The method of claim 1 wherein said biotin biosynthetic enzyme naturally occurs in a bacteria.

7. The transgenic plant tissue of claim 2 wherein said chimeric gene comprises a chloroplast transit peptide signal sequence.

8. The transgenic plant tissue of claim 2 wherein said biotin biosynthetic enzyme naturally occurs in a bacteria.

9. The transgenic plant of claim 3 wherein said chimeric gene comprises a chloroplast transit peptide signal sequence.

10. The transgenic plant of claim 3 wherein said biotin biosynthetic enzyme naturally occurs in a bacteria.

11. The method of claim 1, wherein the amount of a DAP aminotransferase is increased in said plant cell.

12. The method of claim 1, wherein the amount of a biotin synthase is increased in said plant cell.

13. The transgenic plant tissue of claim 2, wherein said chimeric gene encodes a DAP aminotransferase.

14. The transgenic plant tissue of claim 2, wherein said chimeric gene encodes a biotin synthase.

15. The transgenic plant of claim 3, wherein said chimeric gene encodes a DAP aminotransferase.

16. The transgenic plant of claim 3, wherein said chimeric gene encodes a biotin synthase.

* * * * *